US011426578B2

(12) United States Patent
Yang et al.

(10) Patent No.: US 11,426,578 B2
(45) Date of Patent: Aug. 30, 2022

(54) ELECTRODES FOR INTRA-CARDIAC PACEMAKER

(71) Applicant: Medtronic, Inc., Minneapolis, MN (US)

(72) Inventors: Zhongping Yang, Woodbury, MN (US); Becky L. Dolan, Chisago, MN (US); Xin Chen, Blaine, MN (US); Thomas A. Anderson, New Hope, MN (US); Berthold Stegemann, Kassel (DE); Maurice Verbeek, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 16/130,272

(22) Filed: Sep. 13, 2018

(65) Prior Publication Data
US 2019/0083779 A1 Mar. 21, 2019

Related U.S. Application Data

(60) Provisional application No. 62/583,075, filed on Nov. 8, 2017, provisional application No. 62/559,106, filed on Sep. 15, 2017.

(51) Int. Cl.
*A61N 1/05* (2006.01)
*A61N 1/375* (2006.01)
(Continued)

(52) U.S. Cl.
CPC ........... *A61N 1/0573* (2013.01); *A61N 1/368* (2013.01); *A61N 1/3752* (2013.01); *A61N 1/3756* (2013.01); *A61N 1/37512* (2017.08); *A61N 1/0504* (2013.01); *A61N 1/3621* (2013.01); *A61N 1/37518* (2017.08); *A61N 2001/058* (2013.01)

(58) Field of Classification Search
CPC .............. A61N 1/0573; A61N 1/37512; A61N 1/3756; A61N 1/37518; A61N 2001/058
USPC ...................................... 607/9, 126
See application file for complete search history.

(56) References Cited

U.S. PATENT DOCUMENTS 3,814,104 A 6/1974 Irnich et al.
3,943,936 A 3/1976 Rasor et al.
(Continued)

FOREIGN PATENT DOCUMENTS

WO 2002022202 A2 3/2002
WO 2006118865 A2 11/2006
WO 2016171891 A1 10/2016

OTHER PUBLICATIONS

Yang et al., "Implantable Medical Device With Retractable Fixation Sheath", U.S. Appl. No. 15/705,690, filed Sep. 15, 2017, 55 pages.
(Continued)

*Primary Examiner* — John R Downey
(74) *Attorney, Agent, or Firm* — Shumaker & Sieffert, P.A.

(57) ABSTRACT

A pacemaker has a housing and a therapy delivery circuit enclosed by the housing for generating pacing pulses for delivery to a patient's heart. An electrically insulative distal member is coupled directly to the housing and at least one non-tissue piercing cathode electrode is coupled directly to the insulative distal member. A tissue piercing electrode extends away from the housing.

36 Claims, 18 Drawing Sheets

(51) Int. Cl.
*A61N 1/368* (2006.01)
*A61N 1/362* (2006.01)

(56) References Cited

U.S. PATENT DOCUMENTS

| | | | |
|---|---|---|---|
| 4,103,690 A | 8/1978 | Harris | |
| 4,142,530 A | 3/1979 | Wittkampf | |
| 4,269,198 A | 5/1981 | Stokes | |
| 4,280,512 A | 7/1981 | Karr et al. | |
| 4,858,623 A | 8/1989 | Bradshaw et al. | |
| 4,936,823 A | 6/1990 | Colvin | |
| 5,193,540 A | 3/1993 | Schulman et al. | |
| 5,411,535 A | 5/1995 | Fujii et al. | |
| 5,573,540 A | 11/1996 | Yoon | |
| 5,683,447 A | 11/1997 | Bush et al. | |
| 6,007,558 A | 12/1999 | Ravenscroft et al. | |
| 6,151,525 A | 11/2000 | Soykan et al. | |
| 6,240,322 B1 | 5/2001 | Peterfeso et al. | |
| 6,286,512 B1 | 9/2001 | Loeb et al. | |
| 6,409,674 B1 | 6/2002 | Brockway et al. | |
| 6,575,967 B1 | 6/2003 | Leveen et al. | |
| 6,783,499 B2 | 8/2004 | Schwartz | |
| 6,915,149 B2 | 7/2005 | Ben-Haim | |
| 6,978,178 B2 | 12/2005 | Sommer et al. | |
| 7,290,743 B2 | 11/2007 | Nowack | |
| 7,383,091 B1 | 6/2008 | Chitre et al. | |
| 7,418,298 B2 | 8/2008 | Shiroff et al. | |
| 7,532,933 B2 | 5/2009 | Hastings | |
| 8,332,036 B2 | 12/2012 | Hastings | |
| 8,353,940 B2 | 1/2013 | Benderev | |
| 8,478,408 B2 | 7/2013 | Hastings | |
| 8,634,912 B2 | 1/2014 | Bornzin | |
| 8,634,919 B1 | 1/2014 | Hou | |
| 8,700,181 B2 * | 4/2014 | Bornzin | A61N 1/3684 607/126 |
| 8,798,740 B2 | 8/2014 | Samade | |
| 8,914,131 B2 | 12/2014 | Bornzin | |
| 8,923,963 B2 | 12/2014 | Bonner | |
| 8,948,883 B2 | 2/2015 | Eggen | |
| 8,996,109 B2 | 3/2015 | Karst | |
| 9,072,911 B2 | 7/2015 | Hastings | |
| 9,119,959 B2 | 9/2015 | Rys | |
| 9,278,218 B2 | 3/2016 | Karst | |
| 9,393,424 B2 * | 7/2016 | Demmer | A61N 1/36585 |
| 9,393,427 B2 * | 7/2016 | Schmidt | A61N 1/37205 |
| 9,399,139 B2 | 7/2016 | Demmer | |
| 9,399,140 B2 | 7/2016 | Cho | |
| 9,492,668 B2 | 11/2016 | Sheldon | |
| 9,492,669 B2 | 11/2016 | Demmer | |
| 9,526,891 B2 | 12/2016 | Eggen | |
| 9,579,500 B2 | 2/2017 | Rys | |
| 2002/0103424 A1 | 8/2002 | Swoyer et al. | |
| 2002/0165589 A1 | 11/2002 | Imran et al. | |
| 2002/0183817 A1 | 12/2002 | Van Venrooij et al. | |
| 2003/0088301 A1 | 5/2003 | King | |
| 2003/0105501 A1 | 6/2003 | Warman et al. | |
| 2003/0220676 A1 | 11/2003 | Helland | |
| 2004/0147973 A1 | 7/2004 | Hauser | |
| 2004/0230281 A1 | 11/2004 | Heil et al. | |
| 2004/0230283 A1 | 11/2004 | Prinzen | |
| 2006/0084965 A1 | 4/2006 | Young | |
| 2006/0085039 A1 | 4/2006 | Hastings et al. | |
| 2006/0085041 A1 | 4/2006 | Hastings et al. | |
| 2006/0217621 A1 | 9/2006 | Kim et al. | |
| 2006/0235476 A1 | 10/2006 | Gunderson et al. | |
| 2009/0082828 A1 | 3/2009 | Ostroff | |
| 2010/0286626 A1 | 11/2010 | Petersen | |
| 2011/0190842 A1 | 8/2011 | Johnson et al. | |
| 2012/0158111 A1 * | 6/2012 | Khairkhahan | A61N 1/37512 607/127 |
| 2012/0172892 A1 * | 7/2012 | Grubac | A61N 1/05 606/129 |
| 2013/0035748 A1 | 2/2013 | Bonner | |
| 2013/0110127 A1 | 5/2013 | Bornzin | |
| 2013/0123872 A1 * | 5/2013 | Bornzin | A61N 1/37205 607/17 |
| 2013/0138006 A1 * | 5/2013 | Bornzin | A61B 5/283 600/509 |
| 2013/0197609 A1 | 8/2013 | Moore et al. | |
| 2013/0324825 A1 | 12/2013 | Ostroff et al. | |
| 2013/0325081 A1 | 12/2013 | Karst | |
| 2014/0039591 A1 | 2/2014 | Drasler et al. | |
| 2014/0107723 A1 * | 4/2014 | Hou | A61N 1/3756 607/28 |
| 2015/0039070 A1 | 2/2015 | Kuhn et al. | |
| 2015/0051616 A1 * | 2/2015 | Haasl | A61N 1/362 606/129 |
| 2015/0057558 A1 * | 2/2015 | Stahmann | A61N 1/37518 600/510 |
| 2015/0057721 A1 * | 2/2015 | Stahmann | A61N 1/0573 607/60 |
| 2015/0088155 A1 | 3/2015 | Stahmann | |
| 2015/0306378 A1 * | 10/2015 | Schmidt | A61B 6/12 600/424 |
| 2015/0321016 A1 * | 11/2015 | O'Brien | A61N 1/3987 607/62 |
| 2016/0015287 A1 | 1/2016 | Anderson | |
| 2016/0015322 A1 | 1/2016 | Anderson | |
| 2016/0015984 A1 * | 1/2016 | Demmer | A61B 5/686 607/14 |
| 2016/0059002 A1 | 3/2016 | Grubac | |
| 2016/0067486 A1 * | 3/2016 | Brown | A61B 5/316 607/17 |
| 2016/0067490 A1 | 3/2016 | Carney | |
| 2016/0067500 A1 * | 3/2016 | Demmer | A61N 1/3627 607/18 |
| 2016/0114161 A1 | 4/2016 | Amblard | |
| 2016/0114169 A1 * | 4/2016 | Sheldon | A61N 1/3702 607/17 |
| 2016/0144190 A1 * | 5/2016 | Cao | A61N 1/36585 607/17 |
| 2016/0250478 A1 * | 9/2016 | Greenhut | A61N 1/36514 607/17 |
| 2016/0250480 A1 * | 9/2016 | Sheldon | A61N 1/3712 607/19 |
| 2017/0056670 A1 | 3/2017 | Sheldon | |
| 2017/0209689 A1 | 7/2017 | Chen | |
| 2018/0050208 A1 | 2/2018 | Shuros et al. | |
| 2019/0083800 A1 | 3/2019 | Yang et al. | |

OTHER PUBLICATIONS (PCT/US2018/050988) PCT Notification of Transmittal of the International Search Report and the Written Opinion of the International Searching Authority, dated Nov. 14, 2018, 11 pages.

Examination Report from counterpart European Application No. 18779546.3, dated Feb. 26, 2021, 3 pp.

Prosecution History from U.S. Appl. No. 16/130,292, dated Aug. 17, 2020 through Jul. 29, 2021, 46 pp.

Response to European Search Report dated Feb. 26, 2021, from counterpart European application No. 18779546.3, filed Sep. 7, 2021, 11 pp.

Final Office Action from U.S. Appl. No. 16/130,292, dated Oct. 8, 2021, 11 pp.

Advisory Action from U.S. Appl. No. 16/130,292, dated Dec. 13, 2021, 2 pp.

Amendment in Response to Final Office Action dated Oct. 8, 2021, from U.S. Appl. No. 16/130,292, filed Nov. 30, 2021, 21 pp.

Haqqani et al., "The Implantable Cardioverter-Defibrillator Lead: Principles, Progress and Promises," PACE, vol. 32, Oct. 2009, pp. 1336-1353.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the Empower leadless pacemaker and the Emblem subcutaneous ICD," Herzschrittmachertherapie + Elektrophysiologie, vol. 29, Oct. 31, 2018, pp. 355-361.

(56) References Cited

OTHER PUBLICATIONS

Notice of Allowance from U.S. Appl. No. 16/130,292, dated Mar. 28, 2022, 8 pp.

* cited by examiner

ELECTRODES FOR INTRA-CARDIAC PACEMAKER

CROSS-REFERENCE TO RELATED APPLICATIONS

This application claims the benefit of U.S. Provisional Application Ser. No. 62/559,106, filed Sep. 15, 2017, and U.S. Provisional Application Ser. No. 62/583,075, filed Nov. 8, 2017, the entire contents of which are incorporated by reference herein.

TECHNICAL FIELD

The disclosure relates generally to implantable medical devices and in particular to an intra-cardiac pacemaker.

BACKGROUND

The cardiac conduction system includes the sinus atrial (SA) node, the atrioventricular (AV) node, the bundle of His, bundle branches and Purkinje fibers. A heart beat is initiated in the SA node, which acts as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches and Purkinje fibers.

Patients with a conduction system abnormality, e.g., poor AV node conduction or poor SA node function, may receive a pacemaker to restore a more normal heart rhythm and atrioventricular synchrony. Dual chamber pacemakers are available which include a transvenous atrial lead carrying electrodes which are placed in the right atrium and a transvenous ventricular lead carrying electrodes that are placed in the right ventricle via the right atrium. The pacemaker itself is generally implanted in a subcutaneous pocket with the transvenous leads tunneled to the subcutaneous pocket. A dual chamber pacemaker senses atrial electrical signals and ventricular electrical signals and can provide both atrial pacing and ventricular pacing as needed to promote a normal heart rhythm and AV synchrony.

Intracardiac pacemakers have been introduced or proposed for implantation entirely within a patient's heart, eliminating the need for transvenous leads which can be a source of infection or other complications. An intracardiac pacemaker may provide sensing and pacing within a single chamber of the patient's heart. In some patient's single chamber pacing and sensing may adequately address the patient's needs, however single chamber pacing and sensing may not fully address the cardiac conduction disease or abnormalities in all patients. Dual chamber sensing and/or pacing functions may be required to restore a more normal heart rhythm.

SUMMARY

In general, the disclosure is directed to an intracardiac pacemaker. The intracardiac pacemaker includes multiple electrodes coupled to an insulative distal member of the pacemaker housing. In some examples, at least one non-tissue piercing cathode electrode is coupled directly to the insulative distal member and a tissue piercing electrode extends away from the insulative distal member. The non-tissue piercing cathode electrode may be used to sense electrical signals from and deliver electrical pulses to adjacent cardiac tissue. The tissue piercing electrode may be used to sense electrical signals from and deliver electrical pulses to cardiac tissue spaced apart from the adjacent cardiac tissue (i.e., the cardiac tissue adjacent to the non-tissue piercing cathode electrode).

In one example, the disclosure provides a pacemaker including a housing having a proximal end, a distal end and a longitudinal sidewall extending from the proximal end to the distal end and a therapy delivery circuit enclosed by the housing for generating pacing pulses for delivery to a patient's heart. The pacemaker includes an anode electrode defined by an electrically conductive portion of the housing and an electrically insulative distal member coupled to the housing distal end. At least one non-tissue piercing cathode electrode is coupled directly to the insulative distal member and electrically coupled to the therapy delivery circuit for delivering a first portion of the generated pacing pulses via a first pacing electrode vector including the at least one non-tissue piercing cathode electrode and the anode electrode. A tissue piercing electrode extends away from the housing distal end for delivering a second portion of the generated pacing pulses.

In another example, the disclosure provides a pacemaker system including a pacemaker having a housing with a proximal end, a distal end and a longitudinal sidewall extending from the proximal end to the distal end. A therapy delivery circuit is enclosed by the housing for generating pacing pulses for delivery to a patient's heart. An anode electrode is defined by an electrically conductive portion of the housing. An electrically insulative distal member is coupled to the housing distal end. At least one non-tissue piercing cathode electrode is coupled directly to the insulative distal member and electrically coupled to the therapy delivery circuit for delivering at least a portion of the generated pacing pulses via a pacing electrode vector including the at least one non-tissue piercing cathode electrode and the anode electrode. A tissue piercing electrode includes an electrically insulated shaft extending from a distal shaft end to a proximal shaft end that is coupled to the housing distal end and a tip electrode at the distal shaft end. The pacemaker further includes a delivery tool interface member extending from the housing proximal end for receiving a delivery tool for advancing the tip electrode into a first heart chamber tissue for pacing a first heart chamber and advancing the at least one non-tissue piercing cathode along a second heart chamber tissue for pacing a second heart chamber.

In another example, the disclosure provides a method performed by a pacemaker having a housing enclosing a therapy delivery circuit for generating a plurality of pacing pulses. The method includes delivering a first portion of the pacing pulses via at least one non-tissue piercing cathode electrode directly coupled to an insulative distal member coupled to a distal end of the housing to pace a first heart chamber and delivering a second portion of the pacing pulses via a tissue-piercing distal electrode having a cathode tip electrode extending away from the housing distal end to pace a second heart chamber different than the first heart chamber.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
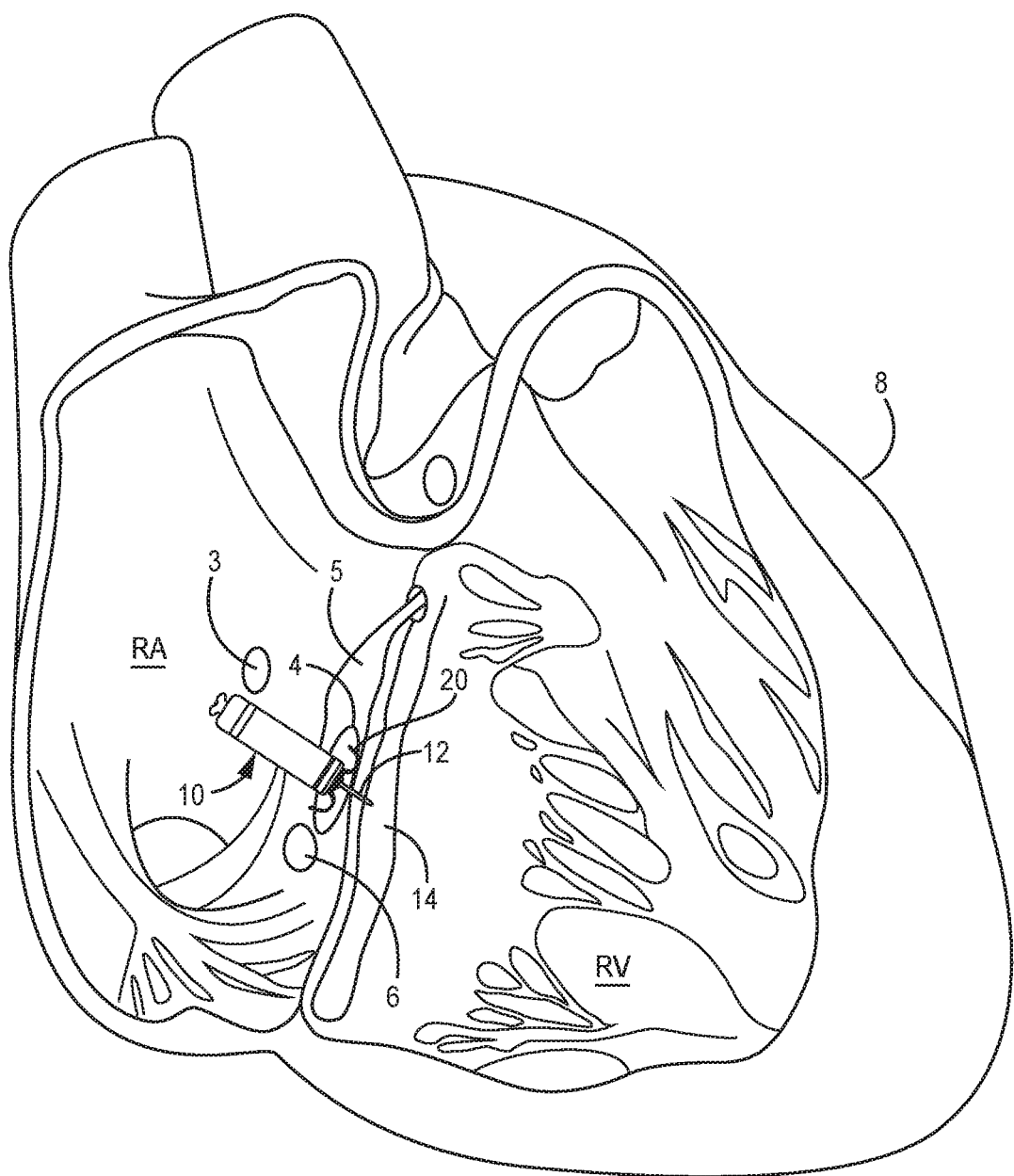
FIG. 1 is a conceptual diagram of a dual chamber intracardiac pacemaker implanted in a patient's heart.

FIG. 1 is a conceptual diagram of a dual chamber intracardiac pacemaker 10 implanted in a patient's heart 8. Pacemaker 10 is shown implanted in the right atrium (RA) of the patient's heart 8 in a target implant region 4. Pacemaker 10 includes a fixation member 20 that anchors a distal end of the pacemaker against the atrial endocardium in the target implant region 4. The target implant region 4 may lie between the Bundle of His 5 and the coronary sinus 6 and may be adjacent the tricuspid valve 3. Pacemaker 10 may be a leadless pacemaker including a dart electrode 12 having a straight shaft extending from the distal end of the pacemaker 10, through the atrial myocardium and the central fibrous body, and into the ventricular myocardium 14 or along the ventricular septum, without perforating entirely through the ventricular endocardial or epicardial surfaces. The dart electrode 12 carries an electrode at the distal end of the shaft for positioning the electrode within the ventricular myocardium for sensing ventricular signals and delivering ventricular pacing pulses. In some examples, the electrode at the distal end of the shaft is a cathode electrode provided for use in a bipolar pacing and sensing electrode pair. While a particular implant region 4 is shown in FIG. 1 to enable an electrode of dart electrode 12 to be positioned in the ventricular myocardium, it is recognized that a pacemaker having the aspects disclosed herein may be implanted at other locations for dual chamber pacing, single chamber pacing with dual chamber sensing, single chamber pacing and/or sensing, or other clinical applications as appropriate.

Figure 2:
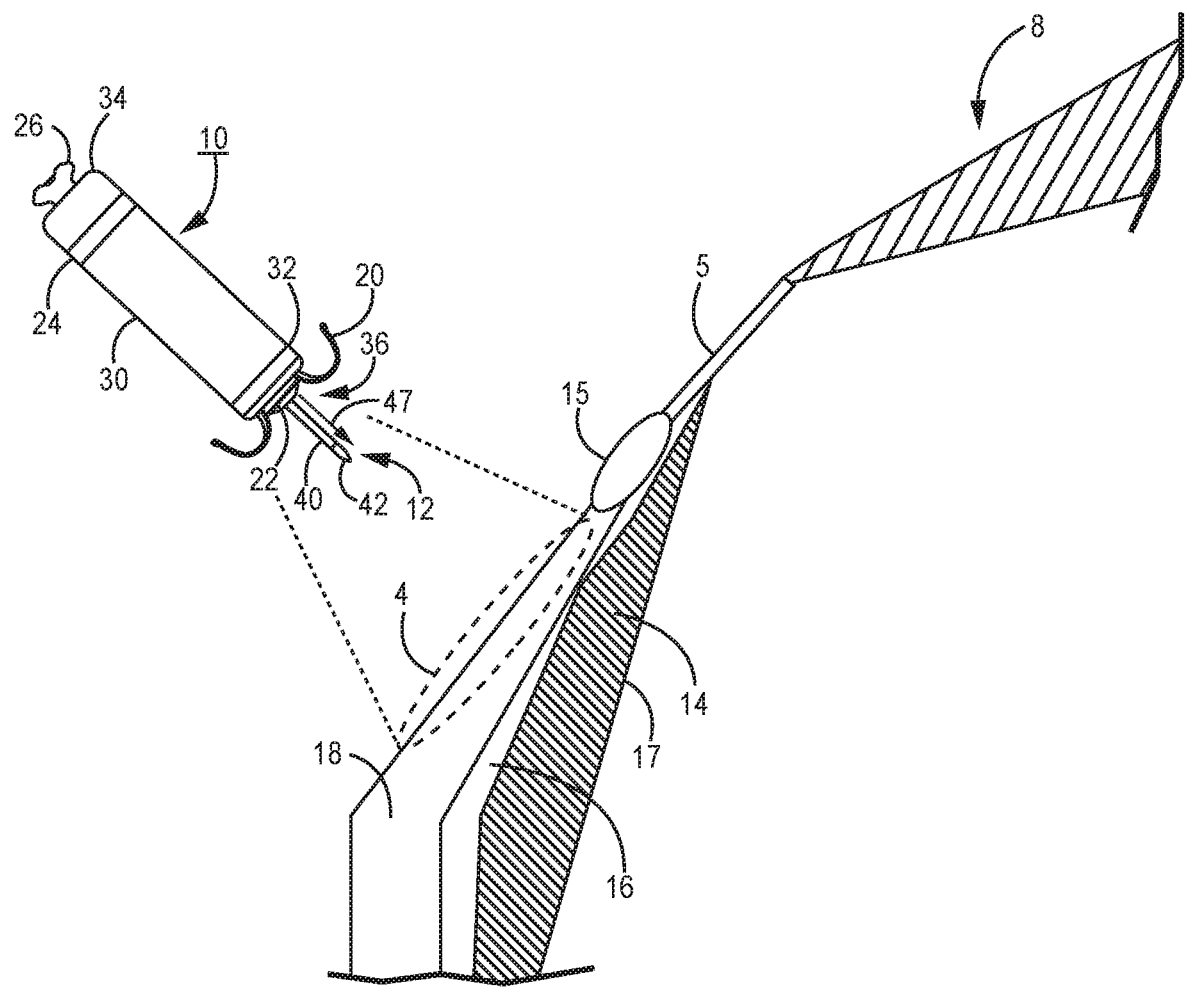
FIG. 2 is an enlarged conceptual diagram of a dual chamber intracardiac pacemaker and anatomical structures of the patient's heart according to one example.

FIG. 2 is an enlarged conceptual diagram of dual chamber intracardiac pacemaker 10 and anatomical structures of the patient's heart 8. Intracardiac pacemaker 10 includes a housing 30 that defines a hermetically sealed internal cavity in which internal components of pacemaker 10 reside, such as a sensing circuit, therapy delivery circuit, control circuit, memory, telemetry circuit, other optional sensors, and a power source as generally described in conjunction with FIG. 14 below. The housing 30 may be formed from an electrically conductive material including titanium or titanium alloy, stainless steel, MP35N (a non-magnetic nickel-cobalt-chromium-molybdenum alloy), platinum alloy or other bio-compatible metal or metal alloy. In other examples, housing 30 is formed from a non-conductive material including ceramic, glass, sapphire, silicone, polyurethane, epoxy, acetyl co-polymer plastics, polyether ether ketone (PEEK), a liquid crystal polymer, or other biocompatible polymer.

Housing 30 extends between a distal end 32 and proximal end 34 and is generally cylindrical in the examples presented herein to facilitate catheter delivery, but housing 30 may be prismatic or other shapes in other examples. Housing 30 may include a delivery tool interface member 26, e.g., at the proximal end 34, for engaging with a delivery tool during implantation of pacemaker 10. One example of a delivery tool that may be used for delivering pacemaker 10 to an implant site is described below in conjunction with FIG. 9.

All or a portion of housing 30 may function as an electrode during pacing and/or sensing. In the example shown, a housing-based electrode 24 is shown to circumscribe a proximal portion of housing 30. When housing 30 is formed from an electrically conductive material, such as a titanium alloy or other examples listed above, portions of housing 30 may be electrically insulated by a non-conductive material, such as a coating of parylene, polyurethane, silicone, epoxy or other biocompatible polymer, leaving one or more discrete areas of conductive material exposed to define proximal housing-based electrode 24. When housing 30 is formed from a non-conductive material, such as a ceramic, glass or polymer material, an electrically-conductive coating or layer, such as a titanium, platinum, stainless steel, or alloys thereof, may be applied to one or more discrete areas of housing 30 to form proximal housing-based electrode 24. In other examples, proximal housing-based electrode 24 may be a component, such as a ring electrode, that is mounted or assembled onto housing 30. Proximal housing-based electrode 24 may be electrically coupled to internal circuitry of pacemaker 10, e.g., via electrically-conductive housing 30 or an electrical conductor when housing 30 is a non-conductive material. In the example shown, proximal housing-based electrode 24 is located nearer to housing proximal end 34 than housing distal end 32 and is therefore referred to as a "proximal housing-based electrode" 24. In other examples, however, a housing-based electrode 24 may be located at other positions along housing 30, e.g., relatively more distally than the position shown.

At distal end 32, pacemaker 10 includes a distal fixation and electrode assembly 36 including fixation member 20 and a dart electrode 12 including shaft 40 extending distally away from housing distal end 32 and carrying tip electrode 42 carried at or near the free, distal end of shaft 40. Tip electrode 42 may have a conical or hemi-spherical distal tip with a relatively narrow tip diameter, e.g., less than 1 mm, for penetrating into and through tissue layers without requiring a sharpened tip or needle-like tip having sharpened or beveled edges that might otherwise produce a cutting action that could lead to lateral displacement of the tip electrode 42 and undesired tissue trauma.

Shaft 40 of dart electrode 12 is a normally straight member and may be rigid in some examples. In other examples, shaft 40 is relatively stiff possessing limited flexibility in lateral directions. Shaft 40 may be non-rigid to allow some lateral flexing with heart motion. However, in a relaxed state, when not subjected to any external forces, shaft 40 maintains a straight position as shown to hold tip electrode 42 spaced apart from housing distal end 32 at least at the height 47 of shaft 40. Dart electrode 12 is configured to pierce through one or more tissue layers to position tip electrode 42 within a desired tissue layer, e.g., the ventricular myocardium. As such, shaft 40 has a height 47 corresponding to the expected pacing site depth and may have a relatively high compressive strength along its longitudinal axis to resist bending in a lateral or radial direction when a longitudinal axial force is applied against tip electrode 42 when pressed against the implant site, e.g., by applying longitudinal pushing force to the proximal end 34 of housing 30 to advance dart electrode 12 into the tissue within the target implant region 4. Shaft 40 may be longitudinally non-compressive. Shaft 40 may be elastically deformable in lateral or radial directions when subjected to lateral or radial forces to allow temporary flexing, e.g., with tissue motion, but returns to its normally straight position when lateral forces diminish. When shaft 40 is not exposed to any external force, or to only a force along its longitudinal central axis, shaft 40 retains a straight, linear position as shown.

Figure 9:
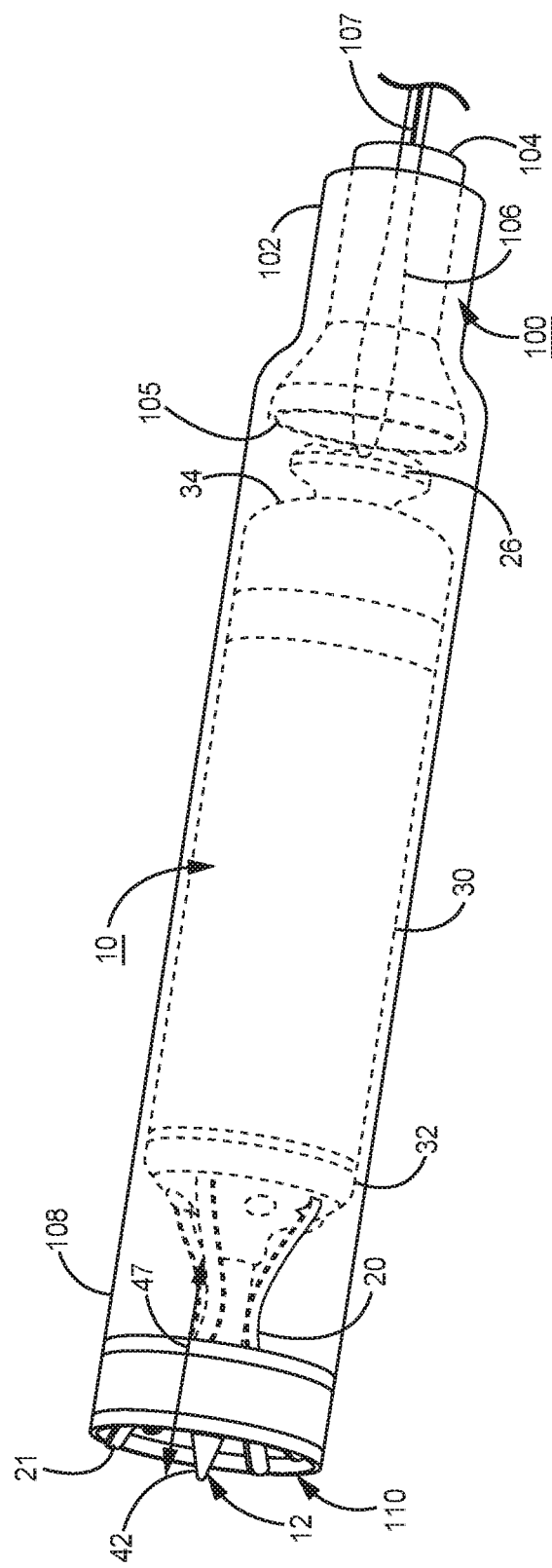
FIG. 9 is a conceptual diagram of the dual chamber intracardiac pacemaker of FIG. 5 loaded in a delivery tool.

Fixation member 20 may include one or more tines having a normally curved position. The tines of fixation member 20 may be held in a distally extended position within a delivery tool as shown in FIG. 9. The distal tips of the fixation member tines penetrate the heart tissue to a limited depth before elastically curving back proximally into the normally curved position (shown) upon release from the delivery tool. Aspects of fixation member 20 may correspond to the fixation member generally disclosed in U.S. 2016/0059002 A1 (Grubac, et al.) or in U.S. Pat. No. 9,119,959 (Rys et al.), both of which are incorporated herein by reference in their entirety.

In some examples, distal fixation and electrode assembly 36 includes a distal housing-based electrode 22. In the case of using pacemaker 10 for dual chamber pacing and sensing, tip electrode 42 may be used as a cathode electrode paired with proximal housing-based electrode 24 serving as a return anode electrode. Alternatively, distal housing-based electrode 22 may serve as a return anode electrode paired with tip electrode 42 for sensing ventricular signals and delivering ventricular pacing pulses. In other examples, distal housing-based electrode 22 may be a cathode electrode for sensing atrial signals and delivering pacing pulses to the atrial myocardium in the target implant region 4. When distal housing-based electrode 22 serves as an atrial cathode electrode, the proximal housing-based electrode 24 may serve as the return anode paired with tip electrode 42 for ventricular pacing and sensing and as the return anode paired with distal housing-based electrode 22 for atrial pacing and sensing.

As shown in FIG. 2, the target implant region 4 in some pacing applications is along the atrial endocardium 18, generally inferior to the AV node 15 and the His bundle 5. The dart electrode 42 is provided with a height 47 of shaft 40 that penetrates through atrial endocardium 18 in the target implant region 4, through the central fibrous body 16 and into ventricular myocardium 14 without perforating through the ventricular endocardial surface 17. When the full height 47 of dart electrode 12 is fully advanced into the target implant region 4, tip electrode 42 rests within ventricular myocardium 14 and distal housing-based electrode 22 is positioned in intimate contact with or close proximity to atrial endocardium 18. Dart electrode 12 may have a total combined height 47 of tip electrode 42 and shaft 40 of approximately 3 mm to 8 mm in various examples. The diameter of shaft 40 may be less than 2 mm and may be 1 mm or less, or even 0.6 mm or less.

In some examples, dart electrode 12 is not provided as a fixation member or having any fixation feature such as a hook, helix, barb or other feature that tends to resist retraction of dart electrode 12 from the tissue at the implant site. Without fixation member 20, dart electrode 12 having a normally straight, linear shaft may easily slide in and out of the heart tissue, at least during the acute phase after implantation. For example, dart electrode 12 may have a normally straight position or shape when not subjected to external forces and be isodiametric from its fixed attachment point at housing distal end 32 to the base of tip electrode 42. Tip electrode 42 may have a maximum diameter at its base that interfaces with shaft 40 with the maximum diameter being isodiametric with shaft 40 (see, for example, FIG. 6). The diameter of tip electrode 40 may decrease from the base toward the distal tip of tip electrode 42, e.g., according to a conical or hemispherical shape of the tip electrode 42. In other examples, tip electrode 42 may be cylindrical with a relatively flat, blunted or rounded tip. The distal tip of tip electrode 42 may be blunted or rounded to avoid a sharp cutting point or edge.

Figure 3:
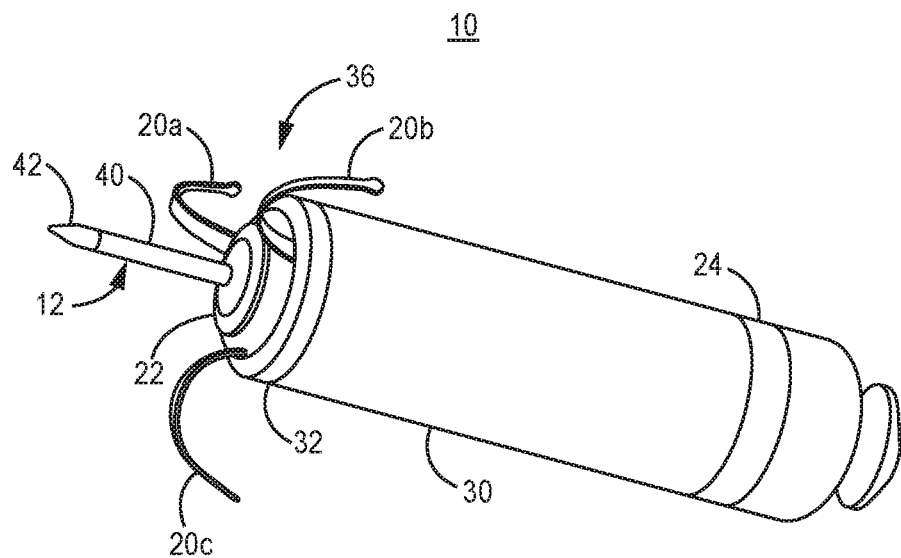
FIG. 3 is a perspective view of a dual chamber intracardiac pacemaker having a distal fixation and electrode assembly that includes a distal housing-based electrode implemented as a ring electrode.

FIG. 3 is a three-dimensional perspective view of intracardiac pacemaker 10 capable of dual chamber pacing and sensing according to one example. Pacemaker 10 has a distal fixation and electrode assembly 36 that includes a distal housing-based electrode 22 implemented as a ring electrode. The distal housing-based electrode 22 is positioned in intimate contact with or operative proximity to atrial tissue when fixation member tines 20a, 20b and 20c of fixation member 20, engage with the atrial tissue. As described below in conjunction with FIG. 9, tines 20a, 20b and 20c, which are elastically deformable, may be extended distally during delivery of pacemaker 10 to the implant site. For example, tines 20a, 20b, and 20c pierce the atrial endocardial surface as the pacemaker 10 is advanced out of the delivery tool and flex back into their normally curved position (as shown) when no longer constrained within the delivery tool. As the tines 20a, 20b and 20c curve back into their normal position, the fixation member 20 acts to pull distal fixation member and electrode assembly 36 toward the atrial endocardial surface. As the distal fixation member and electrode assembly 36 is pulled toward the atrial endocardium, tip electrode 42 is advanced through the atrial myocardium and the central fibrous body and into the ventricular myocardium. Distal housing-based electrode 22 may then be positioned against the atrial endocardial surface.

Distal housing-based electrode 22 may be a ring formed of an electrically conductive material, such as titanium, platinum, iridium or alloys thereof. Distal housing-based electrode 22 may be a single continuous ring electrode. In other examples, portions of the ring may be coated with an electrically insulating coating, e.g., parylene, polyurethane, silicone, epoxy, or other insulating coating, to reduce the electrically conductive surface area of the ring electrode. For instance, one or more sectors of the ring may be coated to separate two or more electrically conductive exposed surface areas of distal housing-based electrode 22. Reducing the electrically conductive surface area of distal housing-based electrode 22, e.g., by covering portions of the electrically conductive ring with an insulating coating, may increase the electrical impedance of distal housing-based 22 and thereby reduce the current delivered during a pacing pulse that captures the myocardium, e.g. the atrial myocardial tissue. A lower current drain conserves the power source, e.g., one or more rechargeable or non-rechargeable batteries, of pacemaker 10.

As described above, distal housing-based electrode 22 may be configured as an atrial cathode electrode for delivering pacing pulses to the atrial tissue at the implant site in combination with the proximal housing-based electrode 24 as the return anode. Electrodes 22 and 24 may be used to sense atrial P-waves for use in controlling atrial pacing pulses (delivered in the absence of a sensed P-wave) and for controlling atrial-synchronized ventricular pacing pulses delivered using tip electrode 42 as a cathode and proximal housing-based electrode 24 as the return anode. In other examples, the distal housing-based electrode 22 may be used as a return anode in conjunction with the cathode tip electrode 42 for ventricular pacing and sensing.

Figure 4:
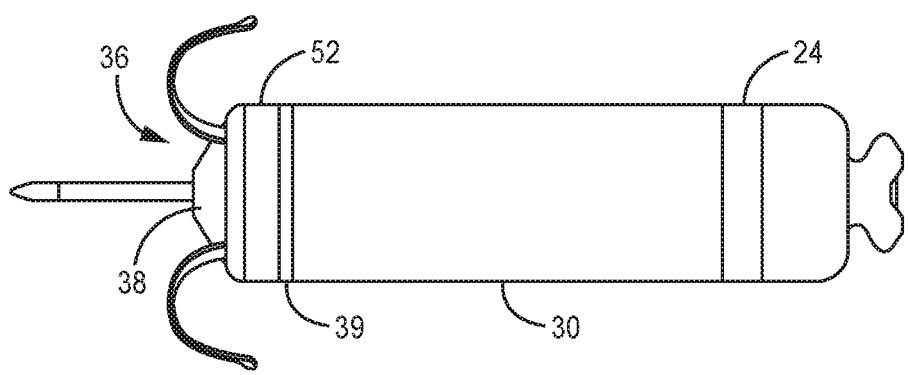
FIG. 4 is a perspective view of dual chamber intracardiac pacemaker according to another example.

FIG. 4 is a side perspective view of intracardiac pacemaker 10 according to another example in which pacemaker 10 may be configured for dual chamber pacing and sensing. In this example, the distal fixation member and electrode assembly 36 carries a distal housing-based electrode 52 that extends circumferentially around the periphery of assembly 36, along circumferential surface 39. In other examples, the distal housing-based electrode 52 may extend circumferentially around housing 30, proximal to the assembly 36 but distal to the proximal housing-based electrode 24 and electrically isolated from proximal housing-based electrode 24. For example, housing 30 may be formed from an electrically non-conductive material, e.g., glass or ceramic, such that two or more housing-based electrodes 22 and 24 may extend circumferentially around housing 30, electrically isolated from one another and individually coupled via respective electrical feedthroughs to electronic circuits, such as sensing and/or pacing circuits, enclosed within housing 30.

In another example, distal fixation member and electrode assembly 36 may include multiple distal housing-based electrodes, e.g., one or more electrodes along its distal surface 38 and/or one or more electrodes along its circumferential surface 39. For example, assembly 36 may include a ring electrode along the distal surface 38 as shown in FIG. 3 or one or more button electrodes along the distal surface 38 as described below in conjunction with FIG. 5, and a ring electrode circumscribing the circumferential surface 39 as shown in FIG. 4. The distal housing-based electrodes may be individually selectable for electrical coupling to sensing and/or pacing circuits enclosed by housing 30 for use individually or in any combination as an electrode having a single polarity or as a combination of electrodes having dual polarity. For example, a single distal housing-based electrode or a combination of single-polarity distal housing-based electrodes may serve as an anode paired with tip electrode 42 serving as the cathode for ventricular pacing. A single distal housing-based electrode or a combination of single-polarity distal housing-based electrodes may serve as an atrial cathode electrode paired with the proximal housing-based electrode 24 serving as the anode. In other examples, a combination of distal housing-based electrodes may be selected as an anode and cathode pair for atrial pacing and sensing.

Figure 5:
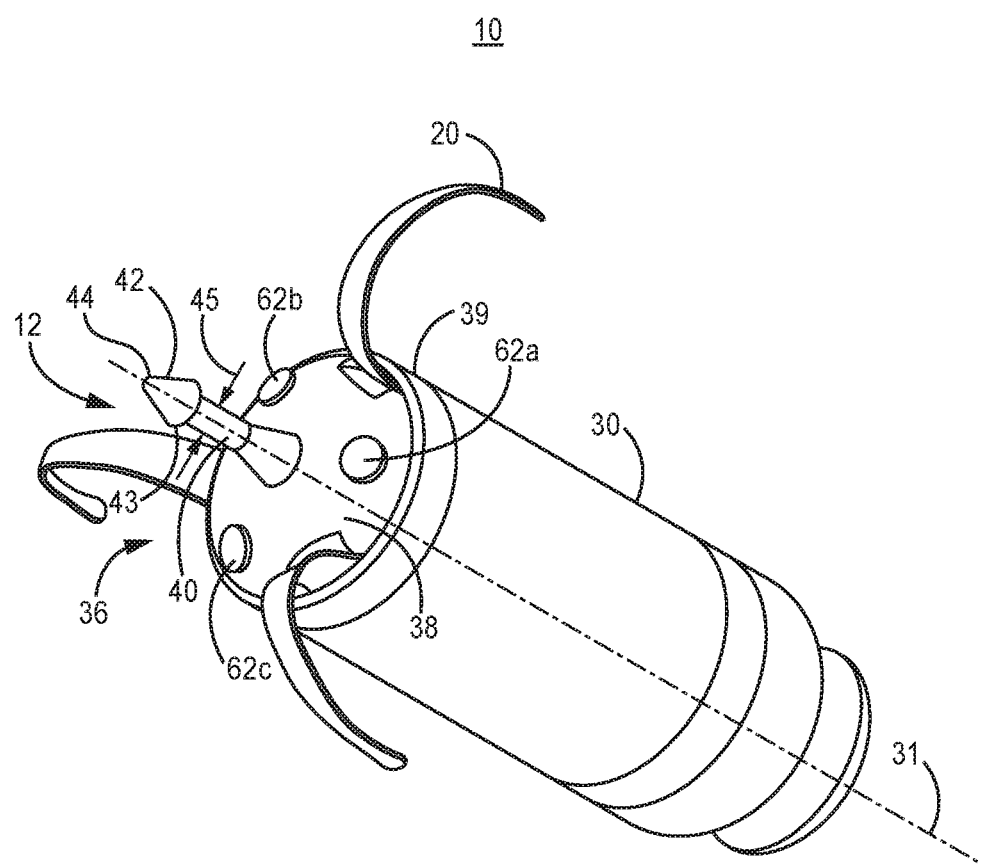
FIG. 5 is a perspective view of dual chamber intracardiac pacemaker according to another example.

FIG. 5 is a three-dimensional perspective view of dual chamber intracardiac pacemaker 10 according to another example. In this example, dart electrode 12 includes a conical tip electrode 42 having a base 43 that has a greater diameter than the outer diameter 45 of shaft 40. The distal tip 44 of tip electrode 42 may be blunted to avoid a sharp tip and high current density at the pacing site.

The distal housing-based electrode 62 includes one or more button electrodes, three button electrodes 62a, 62b and 62c in this example referred to collectively as distal housing-based electrode 62, all positioned along the distal surface 38 of the distal fixation member and electrode assembly 36. The three button electrodes 62a, 62b, and 62c may be electrically coupled together to function as a single electrode. The separate button electrodes 62a, 62b, and 62c may have a total surface area that is smaller than a continuous ring electrode, such as the distal housing-based electrode 22 shown in FIG. 3 or the distal housing-based electrode 52 in FIG. 4. The smaller total surface area of distal housing-based electrode 62 increases the electrical impedance of the pacing load, reducing pacing current and battery drain of pacemaker 10. In one example, the surface area of each button electrode 62a, 62b and 62c is 1.2 square mm or less for a combined total surface area of 3.6 square mm or less.

In other examples, the three button electrodes 62a, 62b, and 62c are individually selectable by switching circuitry included in the electronics enclosed by housing 30. Each electrode 62a, 62b, and 62c may be electrically coupled individually to a pacing circuit and/or a sensing circuit enclosed in housing 30 so that the electrodes 62a, 62b, and 62c can be selected one at a time, two at a time, or all three at a time, e.g., to serve as an atrial cathode electrode for sensing atrial signals and delivering atrial pacing pulses.

The separate button electrodes 62a, 62b and 62c may be distributed at equal distances along distal surface 38, peripherally to dart electrode 12, which is centered co-axially with the longitudinal axis 31 of housing 30. For instance, the arc separating each adjacent pair of electrodes 62a, 62b, and 62c may be 120 degrees. When distal surface 38 is pulled against the atrial endocardium by fixation member 20, one or two of electrodes 62a, 62b and 62c may have better contact with the atrial endocardium than the other one or two of electrodes 62a, 62b and 62c depending on the anatomy at the implant site and the angle of entry of dart electrode 12 and fixation member 20 at the implant site. By spacing apart electrodes 62a, 62b, and 62c along the distal surface 38, e.g., at different radial locations, at least one electrode 62a, 62b and 62c is expected to have good contact with the endocardium for achieving reliable atrial sensing and pacing.

Electrodes 62a, 62b and 62c are shown spaced between a like-number of tines of fixation member 20 in FIG. 5. Each electrode 62a, 62b and 62c is approximately centered between two adjacent tines of fixation member 20. In other examples, each electrode 62a, 62b and 62c may be radially aligned with a tine of fixation member 20 to promote intimate contact between the endocardial surface and the electrodes 62a, 62b and 62c. While three button electrodes 62a, 62b and 62c are shown in FIG. 5, it is recognized that the distal housing-based electrode 62 may comprise less than three, as few as one, or more than three button electrodes distributed along the distal surface 38 of fixation member and electrode assembly 36 at equal or non-equal intervals or arcs. Furthermore, distal fixation member and electrode assembly 36 is not required to have an equal number of electrodes defining distal housing-based electrode 62 and tines included in fixation member 20; fewer or more electrodes may be provided along distal surface 38 than the number of fixation member tines.

The electrodes 62a, 62b and 62c may be raised as shown in FIG. 5 such that the surfaces of the electrodes 62a, 62b and 62c protrude from the distal surface 38 for making better contact with the atrial endocardium at the implant site. In other examples, the electrodes 62a, 62b and 62c may be flush with distal surface 38. Distal surface 38 is shown as a convex surface. In other examples distal surface 38 may be more or less convex than shown here and may be adapted to match the anatomy at the implant site to promote contact of the distal housing-based electrode 62 with the atrial endocardium. In still other examples, one or more button electrodes 62a, 62b and 62c may be positioned along the circumferential surface 39 of assembly 36.

Figure 6:
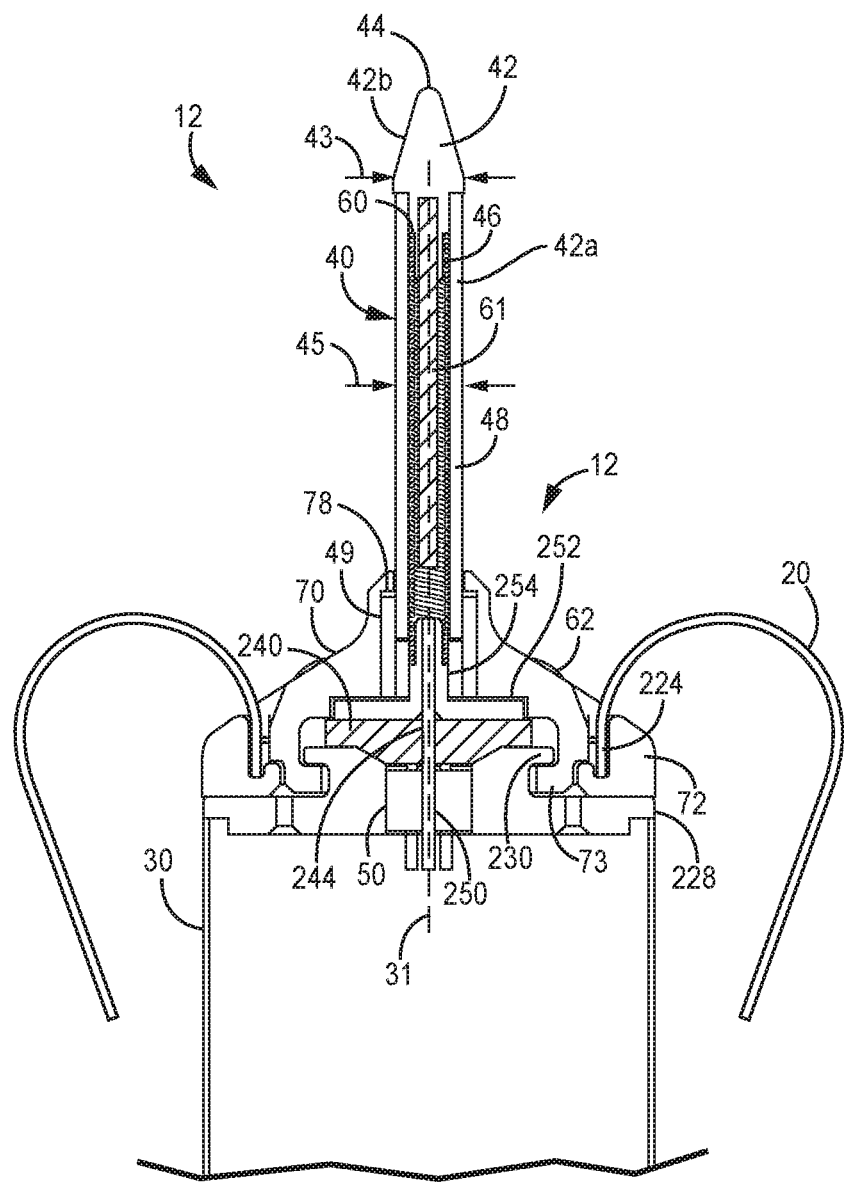
FIG. 6 is a sectional view of a distal portion of the dual chamber intracardiac pacemaker of FIG. 5.

FIG. 6 is a sectional view of a distal portion of intracardiac pacemaker 10, capable of dual chamber pacing and sensing. In some examples, distal fixation member and electrode assembly 36 includes an inner body 70 and outer ring 72 for supporting and retaining fixation member 20, dart electrode 12, and distal housing-based electrode 62 and coupling these components to housing 30 (and its internal components as needed). A method of assembling these various components is described below in conjunction with FIGS. 12A-12C. Fixation member 20 may include one or more curving tines that extend from a fixation member ring 224 that is retained between interlocking faces of inner body 70 and outer ring 72. Inner body 70 and outer ring 72 may be molded components including polyurethane, silicone, epoxy, PEEK, polyethylene, or other biocompatible polymer materials and may include various conduits, lumens, cavities, grooves or other features for receiving and retaining shaft 40, housing-based electrode 62, electrical conductors and other assembly components as needed. Other aspects of distal fixation member and electrode assembly 36 are described below in conjunction with FIGS. 12A-12C.

In this example, shaft 40 includes an electrical conductor 46 electrically coupled to and extending from tip electrode 42 to an electrical feedthrough wire 250 that provides electrical connection across housing 30 via electrical feedthrough 50. The electrical conductor 46 is shown as a coiled conductor in this example but may be a braided, twisted or other multi-filar conductor or single strand wire in other examples. Shaft 40 further includes a tubular body 48 that electrically insulates electrical conductor 46 and, in conjunction with electrical conductor 46, provides shaft 40 with the mechanical properties of a high compressive strength along its longitudinal central axis 31 and, in some examples, lateral elastic deformability. Dart electrode 12 possesses high compressive strength so that it can penetrate into and through tissue layers with little or no compression or flexing due to longitudinal forces against tip electrode 42. Dart electrode 12 may possess some flexibility in lateral directions when subjected to lateral forces due to heart motion. Tubular body 48 may be a coating or overmolded component that is applied over electrical conductor 46 to enclose and circumscribe conductor 46. In some examples, tubular body 48 may become bonded to electrical conductor 46 during the overmolding process. In other examples, tubular body 48 may be a pre-formed, extruded or molded tubular component that receives electrical conductor 46 during the assembly process. Tubular body 48 may be an electrically insulating material and may include parylene, polyurethane, epoxy, PEEK, silicone or other biocompatible polymers. In other examples, tubular body 48 may be an electrically conductive material, e.g., stainless steel, titanium or titanium alloy, with its outer exposed surface coated with an electrically insulating material.

Tip electrode 42 includes a shank portion 42a and an active, exposed electrode portion 42b that is exposed at the distal end of shaft 40. Shank portion 42a may be unexposed to the surrounding tissue/environment and is electrically coupled to electrical conductor 46 and mechanically coupled to shaft 40. For example, shank portion 42a may extend through at least a portion of an inner lumen 60 defined by tubular body 48 and coiled electrical conductor 46 and may extend further than shown, e.g., half or even all of the way to inner body 70. In other examples, shank portion 42a is a tubular member that extends into tubular body 48 and receives a portion of electrical conductor 46 within an inner lumen defined by shank portion 42a for both mechanical and electrical coupling between conductor 46 and tip electrode 42. Shank portion 42a may contribute to the mechanical properties of dart electrode 12 of being longitudinally non-compressible and, at least in some examples, being laterally elastically deformable.

If needed, a central member 61 may extend within lumen 60 to achieve the desired mechanical properties of dart electrode 12 being longitudinally non-compressible and laterally elastically deformable. Central member 61 may be a solid support member, a spring, a cable, a tube or rod and may include a metal or plastic material that provides high longitudinal compression strength and/or lateral elastic deformability. In other examples, central member 61 may be a steroid-impregnated polymer member that provides steroid elution over time through the exposed tip electrode portion 42b. For example, central member 61 may be a monolithic controlled release device (MCRD) including a polymer matrix, e.g., a silicone or polyurethane base, and a steroid, e.g., sodium dexamethasone phosphate, compounded in the polymer matrix.

The active electrode portion 42b of tip electrode 42 is exposed at the distal end of shaft 40 and is shown as substantially conical with a rounded or blunted tip 44, as opposed to having a sharpened tip that may be damaging to surrounding tissue or create a point of high current density during pacing. The exposed electrode portion 42b has a base 43 that is isodiametric with the outer diameter 45 of tubular body 48. In this way, dart electrode 12 slides into the heart tissue at the desired implant site with minimized resistance and may be easily be retracted from the implant site if pacemaker 10 ever needs to be removed.

Exposed electrode portion 42b may be sintered, e.g., sintered platinum iridium. Tip electrode 42 may be a steroid-eluting electrode having a sintered active electrode portion 42b and a hollow, tubular shank portion 42a that allows steroid eluting from a steroid eluting member, e.g., central member 61 in some examples, to be released through tip electrode 42 into surrounding tissue to reduce the foreign body response at the pacing and sensing site.

Shaft 40 may include a base 49 that circumscribes tubular body 48 and is retained within inner body 70. Base 49 provides mechanical support to a welded, electrical connection between electrical conductor 46 and feedthrough wire 250. In some examples, feedthrough wire 250 is welded to a shaft receiving pin 254 of a shaft mounting member 252. Shaft mounting member 252 may be an electrically conductive member that is electrically coupled to conductor 46 by mounting shaft 40 over shaft receiving pin 254 of shaft mounting member 252. The physical contact of the electrically conductive shaft receiving pin 254 and electrical conductor 46 may provide electrical connection between electrical conductor 46 and feedthrough wire 250, which is welded or otherwise electrically coupled to shaft mounting member 252. Base 49 of shaft 40 provides electrical insulation and mechanical support to these connections. Base 49 may be a polymer tubular member that is sealed and bonded to the outer tubular body 48 of shaft 40, e.g., using medical adhesive. Base 49 may rest against an interior stopping surface 78 of inner body 70 to prevent dart electrode 12 from being pulled away from inner body 70.

Shaft mounting member 252 is mounted on a manifold 240 that directs feedthrough wire 250 toward dart electrode 12 and other feedthrough wires (not shown in FIG. 6) to distal housing-based electrode 62. Manifold 240 includes a central lumen 244 that passes feedthrough wire 250 from electrical feedthrough 50 to shaft mounting member 252. Manifold 240 may be adhesively bonded to the distal end cap 228 of housing 30 and over feedthrough 50.

Figure 12A:
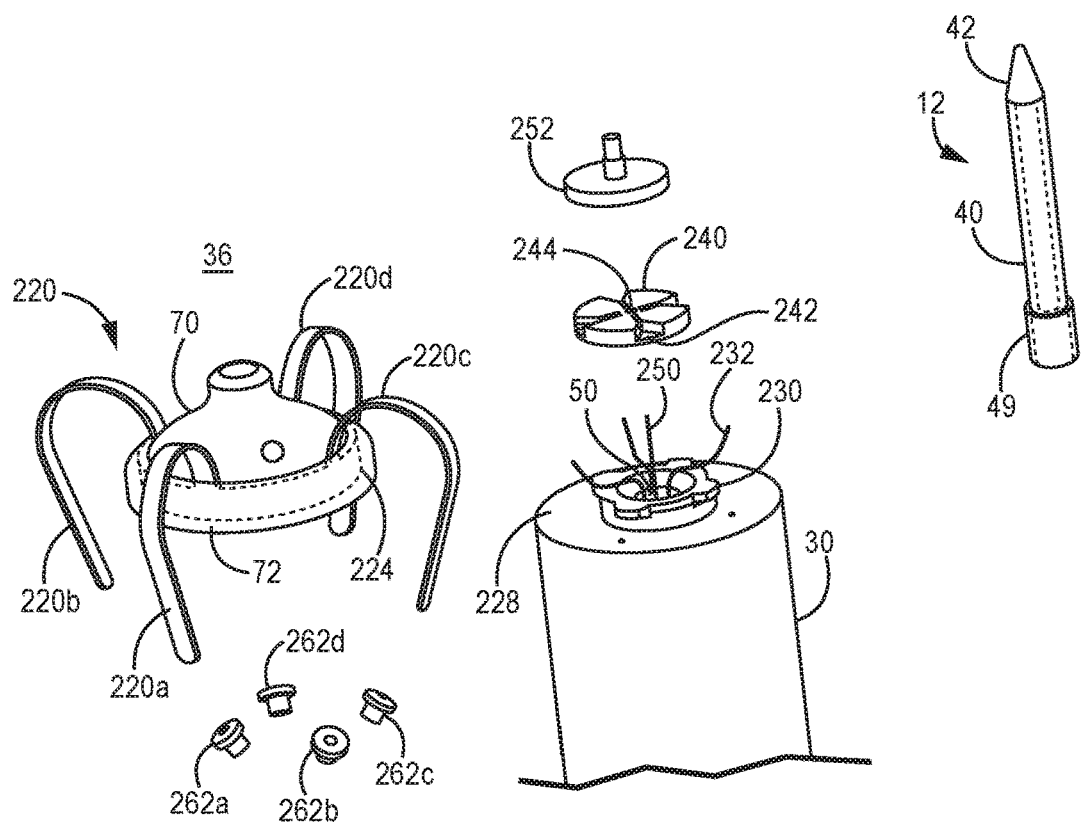
FIGS. 12A-12C are conceptual diagrams of components for assembling the distal fixation member and electrode assembly of the intracardiac pacemaker according to one example.

Distal end cap 228 may include one or more interior, radially-outward extending tabs 230. Inner body 70 may include one or more radially-inward extending tabs 73 that engage and mate with respective outward extending tabs 230. During assembly, inner body 70 may be adhesively bonded to outer ring 72 with fixation member ring 224 trapped between inner body 70 and outer ring 72 to form a subassembly. The subassembly may be assembled with the dart electrode 12 and then attached to housing distal end cap 228 by seating inner body 70 onto distal end cap 228 with inward extending tabs 73 positioned between outward extending tabs 230, within spaces defined by spaced apart outward extending tabs 230 (as best seen in FIG. 12A). Once seated against distal end cap 228, the entire fixation member and electrode assembly 36 may be rotated relative to housing 30 (and housing distal end cap 228) such that radially inward extending tabs 73 of inner body 70 become entrapped underneath radially outward extending tabs 230 of distal end cap 228. Medical adhesive may be used to fill and seal any gaps or spaces and bond the various interfacing surfaces of the distal fixation member and electrode assembly 36 and housing 30. In this way, distal fixation member and electrode assembly 36 may be fixedly coupled to housing 30.

Figure 7:
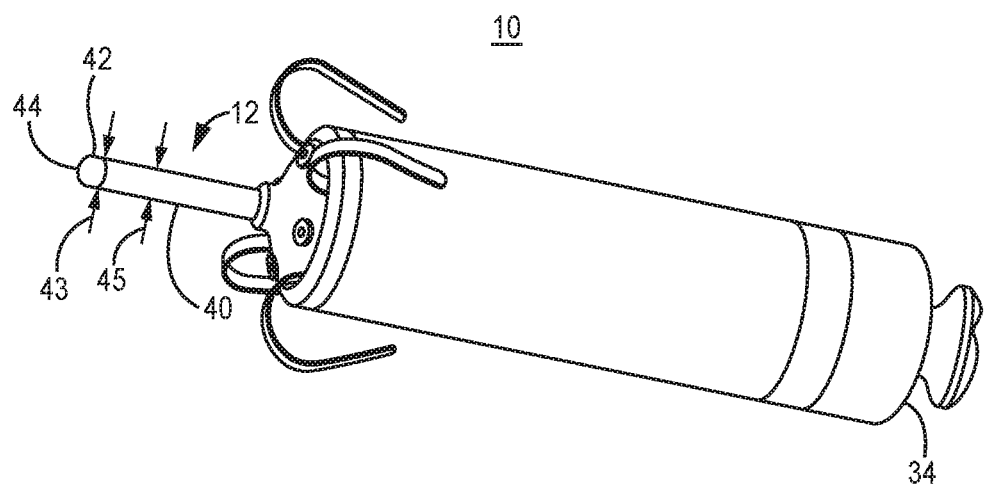
FIG. 7 is a perspective view of an intracardiac pacemaker according to yet another example.

FIG. 7 is a side perspective view of pacemaker 10 according to another example. In this example, dart electrode 12 includes a rounded, cylindrical tip electrode 42 instead of a conical tip electrode as shown in FIG. 6. The distal tip 44 of tip electrode 42 is made a blunt as possible, with rounded edges, to avoid any tissue cutting action and points of high current density. As diameter of base 43 increases (or the diameter 45 of shaft 40 increases), the diameter at tip 44 may need to decrease or become more pointed, e.g., as shown by the conical shape of tip electrode 42 in FIG. 6, in order to penetrate the heart tissue with a force that is reasonably achievable during surgical implantation. For example, the larger and more blunt tip 44 becomes, the greater the force required to advance dart electrode 12 into and through the atrial myocardium and central fibrous body to position tip electrode 42 in the ventricular myocardium. The smaller the diameter 45 of shaft 40 and isodiametric base 43 of tip electrode 42 are, the more rounded or blunt distal tip 44 can be while still enabling penetration and advancement through the heart tissue. The longitudinal force applied to dart electrode 12 may be applied at the housing proximal end 34 by a user manipulating a delivery tool and/or by the pulling force of fixation member 20 as it elastically flexes from an extended position back to its normally curved position.

Figure 8:
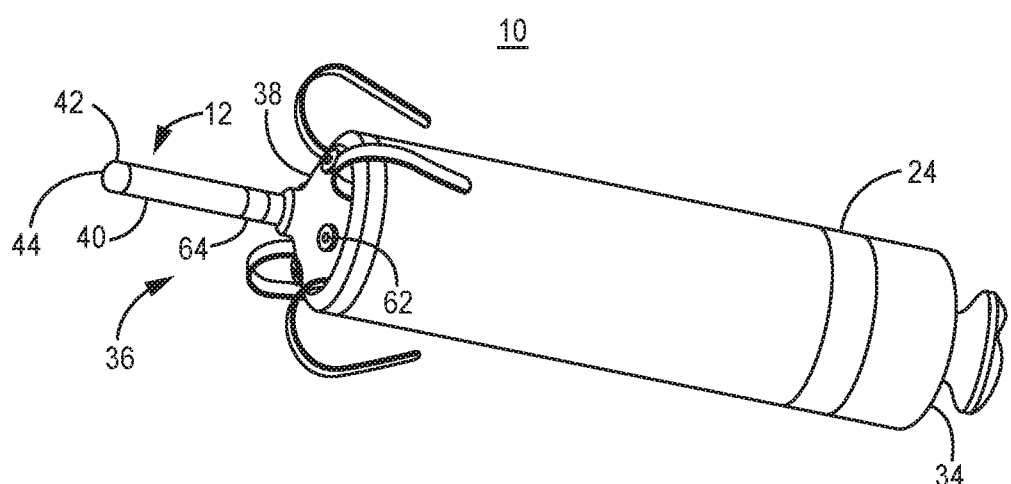
FIG. 8 is a perspective view of a dual chamber intracardiac pacemaker having a second electrode carried by the dart electrode according to another example.

FIG. 8 is a side perspective view of dual chamber intracardiac pacemaker 10 according to another example. In the examples described above, shaft 40 of dart electrode 12 has an outer tubular body 48 (see FIG. 6) that is electrically non-conductive and insulates the electrical conductor 46 that electrically couples tip electrode 42 to the circuitry enclosed by housing 30. The active tip electrode portion 42b is the only electrically conductive surface of dart electrode 12 that is exposed to the surrounding tissue/environment. In the example shown in FIG. 8, dart electrode 12 includes a second electrode 64 carried by shaft 40. Second electrode 64 may be a ring electrode that is mounted around shaft 40 or mounted between shaft 40 and the distal surface 38 of fixation member and electrode assembly 36. In one example, tip electrode 42 and second (ring) electrode 64 of dart electrode 12 are coupled to respective coiled, braided, twisted, stranded or wire conductors and the conductors are overmolded with an electrically insulating coating to form tubular body 48, leaving the active surface areas of electrodes 42 and 64 exposed.

In other examples, the tubular body of shaft 40 may be an electrically conductive metal body having an insulating coating, e.g., parylene or other examples given herein, covering its outer surface except for the exposed area of electrode 64 and insulating shaft 40 from tip electrode 42. The insulating coating insulates electrodes 42 and 64 from each other so that they may serve as mutually exclusive electrodes.

The second electrode 64 carried by shaft 40 may serve as an anode electrode paired with tip electrode 42 serving as a cathode for delivering ventricular pacing pulses and sensing ventricular signals. For instance, the second electrode 64 carried by shaft 40 may be electrically coupled to housing 30 or electrical ground via an insulated conductor extending from shaft 40, through fixation member and electrode assembly 36. In other examples, the second electrode 64 may be a cathode electrode and tip electrode 42 may be an anode electrode.

In other examples, the second electrode 64 may function as an atrial cathode electrode and be electrically coupled to an atrial sensing channel and an atrial pacing channel of respective sensing and pacing circuits enclosed by housing 30. In this case, the tip electrode 42 may serve as a ventricular electrode, e.g., a cathode electrode, and the ring electrode 64 provided as a second electrode along shaft 40 proximal to tip electrode 42 may serve as an atrial electrode, e.g., an atrial cathode electrode. In this example, each cathode electrode, tip electrode 42 and ring electrode 64, may be paired with the same or different anode electrodes, which may be carried along distal surface 38 of fixation member and electrode assembly 36, such as distal housing-based electrode 62 provided as a button electrode, a ring electrode circumscribing fixation member and electrode assembly 36 (such as electrode 52 shown in FIG. 4), or the proximal housing-based electrode 24.

FIG. 9 is a conceptual diagram of dual chamber intracardiac pacemaker 10 loaded in a delivery tool 100. Delivery tool 100 includes an outer catheter 102, advancement tool 104, tether 106 and may include an inner steering tool 107. Outer catheter 102 has a distal device receptacle 108 for receiving and retaining pacemaker 10. Receptacle 108 has a distal opening 110 through which pacemaker 10 may be loaded into delivery tool 100 and released from delivery tool 100 at an implant site. Advancement tool 104 extends through an inner lumen of outer catheter 102 and may include a distal pusher cone or cup 105 configured to interface with the proximal end 34 of housing 30 for advancing housing 30 out distal opening 110 when advancement tool 104 is advanced distally through outer catheter 102. A tether 106, which may be provided as an elongated body or suture, may extend through advancement tool 104 and be removably attached or looped through the delivery tool interface 26 of pacemaker 10. Tether 106 may be used by a clinician to retract on pacemaker 10 to retain pacemaker 10 within receptacle 108 during advancement of the delivery tool 100 to an implant site.

Inner steering tool 107 may be an elongated tubular body that extends through a lumen defined by advancement tool 104. Inner steering tool 107 may be a steerable body that can be used to steer distal opening 110 to the target implant region 4 (shown in FIG. 1). In some examples, inner steering tool 107 may define an inner lumen through which a steering member such as a guide wire extends. In this case, inner steering tool 107 may be a passive tubular body that follows the contour of the inner steering member or guidewire.

Pusher cup 105 is sized to mate and removably engage with the housing proximal end 34 and delivery tool interface member 26. Tether 106 may be used to retract and retain pacemaker 10 in receptacle 108 as long as advancement tool 104 remains in a retracted position (as shown) within outer catheter 102. When distal opening 110 has been steered to a desired implant site, tension on tether 106 may be lessened as advancement tool 104 is advanced distally in outer catheter 102 such that pusher cup 105 advances distally through receptacle 108, pushing pacemaker 10 out of distal opening 110.

Fixation member 20 is shown held in an extended position within the confines of receptacle 108. When distal opening 110 is placed near or against the endocardial tissue at a target implant region, e.g., region 4 of FIG. 1, and pacemaker 10 is pushed out of distal opening 110 by advancement tool 104, the distal tip 21 of each tine of fixation member 20 pierces the atrial endocardial surface and advances partially into the myocardial tissue until the fixation member 20 is advanced far enough out of receptacle 108 that the preformed curved tines of fixation member 20 are no longer confined and begin to elastically curve or bend back into their normally relaxed, curved position. After deployment of fixation member 20, tether 106 may be retracted to be released from delivery tool interface member 26, and delivery tool 100 may be retracted and removed leaving pacemaker 10 actively fixed at the implant site. Aspects of the delivery tool 100 and fixation member 20 may correspond to the medical device fixation apparatus and techniques generally disclosed in pending U.S. Patent Publication No. 2012/0172892 (Grubac, et al.), incorporated herein by reference in its entirety.

Figure 10:
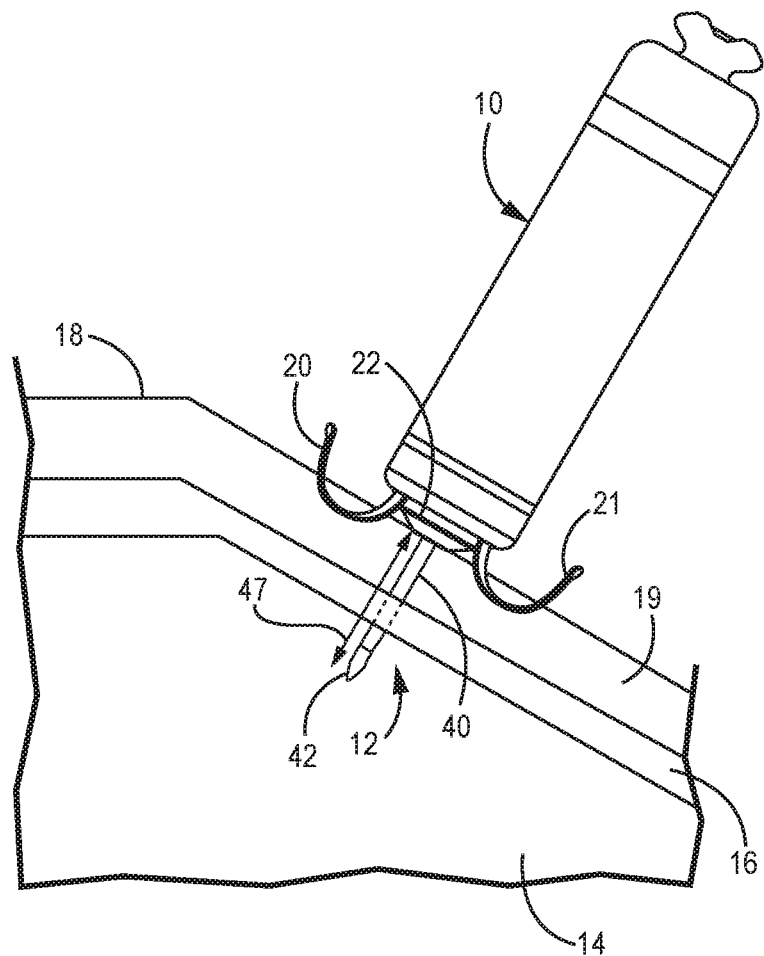
FIG. 10 is a conceptual diagram of an intracardiac pacemaker implanted at a target implant site.

FIG. 10 is a conceptual diagram of pacemaker 10 implanted at a target implant site. As shown in the implanted position of FIG. 10, the distal tip 21 of each tine of fixation member 20 may exit back out of the atrial endocardial surface 18 such that tissue becomes engaged within the curved portion of each tine of fixation member 20. As fixation member 20 becomes engaged with the atrial myocardium 19, dart electrode 12 pierces into the tissue at the target tissue region and advances through the atrial myocardium 19 and central fibrous body 16 to position tip electrode 42 in the ventricular myocardium 14 as shown in FIG. 10. The distal housing-based electrode 22, shown as a ring electrode in FIG. 10, may be held in contact with the atrial endocardial surface 18 by fixation member 20. Retraction of dart electrode 12 out of the ventricular myocardium 14 is prevented by fixation member 20. As described above, dart electrode 12 may be linear and isodiametric from the conical, cylindrical or hemispherical tip electrode 42 to its attachment point on the distal surface of the fixation member and electrode assembly 36 such that there are no protrusions, hooks, barbs, helices or other features that would resist retraction of dart electrode 12. Fixation member 20 is the sole fixation feature of pacemaker 10 in some examples.

The height 47 of dart electrode 12 is selected to ensure tip electrode 42 reaches an adequate depth in the tissue layers to reach the targeted pacing and sensing site, in this case in the ventricular myocardium, without puncturing all the way through into an adjacent cardiac chamber. Height 47 may be at least 3 mm but is less than 20 mm, less than 15 mm, less than 10 mm or up to 8 mm in various examples.

Referring again to FIG. 9, tip electrode 42 and distal tip 21 of each tine of fixation member 20 in the extended position may extend approximately equidistant from housing distal end 32. The tines of fixation member 20 in the extended position shown in FIG. 9 and dart electrode 12 may extend to the same height 47 from the connection point of shaft 40 to assembly 36. In this case, tip electrode 42 and tine distal tips 21 of fixation member 20 will pierce the tissue at the implant site simultaneously as pacemaker 10 is advanced out distal opening 110. Manual pressure applied to the housing proximal end 34 via advancement tool 104 provides the longitudinal force required to pierce the cardiac tissue at the implant site.

In other examples, the tine distal tip 21 may extend a height from the proximal base of shaft 42 that is greater than the height 47 of dart electrode 12 when fixation member 20 is held in the extended position within receptacle 108. Distal tine tips 21 pierce the tissue first in this case, before tip electrode 42, and may act to pull pacemaker 10 toward the atrial endocardial surface 18 as fixation member elastically bends or curves back into its normally curved position. This pulling force produced by fixation member 20 may contribute to the longitudinal force that drives tip electrode 42 into the tissue at the implant site and advances tip electrode 42 to the ventricular pacing site. In some examples, the pulling force produced by fixation member 20 may be the only force required to drive dart electrode 12 into the heart tissue to a desired depth in the ventricular myocardium to achieve dual chamber pacing and sensing functionality.

In still other examples, the height 47 of dart electrode 12 may be greater than the distance that tine distal tips 21 extend when held in the extended position shown in FIG. 9. In this case, the tip electrode 42 pierces the atrial endocardium first and advances partially into the tissue layers before the tine distal tips 21 of fixation member 20 enter the endocardial tissue. For instance, tip electrode 42 may advance at least partially through the atrial myocardium and the fixation member 20 may act to increase the longitudinal force driving tip electrode 42 through the central fibrous body and into the ventricular myocardium by pulling pacemaker 10 toward the atrial endocardial surface as the tines of fixation member 20 elastically return to their normally curved position.

Figure 11:
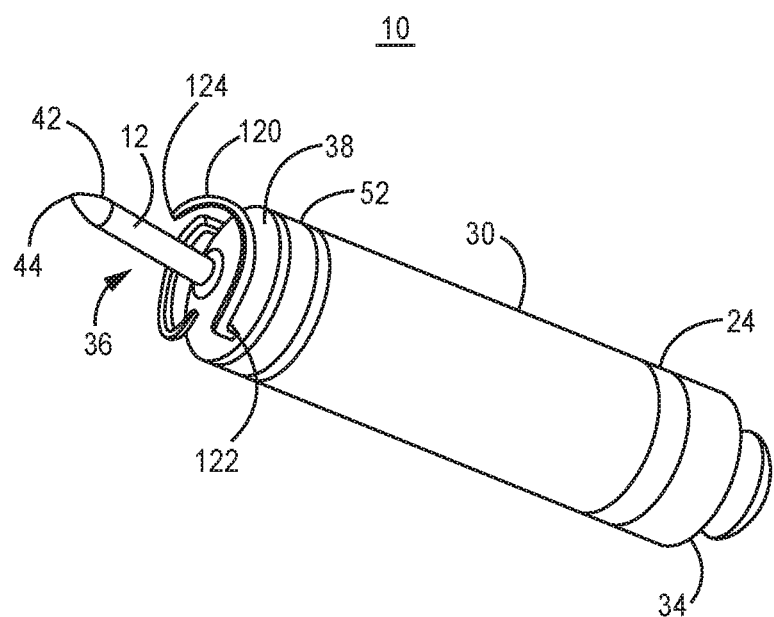
FIG. 11 is a perspective view of a dual chamber intracardiac pacemaker having an alternative fixation member.

FIG. 11 is a three-dimensional perspective view of an intracardiac pacemaker 10 having an alternative fixation member 120. The intracardiac pacemaker 10 may be dual chamber pacemaker having a distal dart electrode 12 for pacing and sensing in the ventricular myocardium may be anchored in an atrial chamber using other fixation members than the elastically-deformable, tissue penetrating tines shown in example of fixation member 20 given above. In the example of FIG. 11, fixation member 120 includes two tissue engaging portions that extend from a fixed end 122 attached to fixation member and electrode assembly 36 to a tissue-piercing distal tip 124 along a peripheral, helical path. Fixation member 120 may generally correspond to the tissue engaging portions of the electrode assembly disclosed in U.S. Pat. No. 8,948,883 (Eggen, et al.), incorporated herein by reference in its entirety.

Pacemaker 10 may be implanted at a tissue site by advancing dart electrode 12 into the tissue, e.g., the atrial myocardium, by applying force along the center, longitudinal axis of housing 30 and dart electrode 12 using an advancement tool, such as the advancement tool 104 shown in FIG. 9. In other examples, an axial force along the longitudinal center axis of housing 30 and dart electrode 12 may be applied while also applying a rotational force using the delivery tool, e.g., by rotating advancement tool 104 or the entire delivery tool 100, to advance dart electrode 12 into the implant site by both rotation and axial force. When the piercing distal tip 124 of fixation member 120 reaches the tissue surface, e.g., the atrial endocardial surface, pacemaker 10 is rotated (clockwise for the orientation of the tissue engaging portions shown) to advance fixation member 120 into the tissue site and further advance dart electrode 12 to the ventricular sensing and pacing site. The engagement and advancement of fixation member 120 into the tissue at the implant site may contribute to the longitudinal force that advances dart electrode 12 through the tissue layers and into the ventricular myocardium. Fixation member 120 prevents retraction of dart electrode 12 from the ventricular pacing site.

Dart electrode 12 is shown having a height that extends a greater distance from distal surface 38 than the distal piercing tips 124 of fixation member 120. In other examples, the tissue engaging portions of fixation member 120 may have a greater length than shown in FIG. 11 such that distal piercing tips 124 and the tip 44 of tip electrode 42 are equidistant from distal surface 38 and enter the tissue simultaneously. Alternatively, distal piercing tips 124 may extend to a height from distal surface 38 beyond the height of dart electrode 12. In this case, rotation of pacemaker 10 advances fixation member 120 into the cardiac tissue at the implant site first, and then dart electrode 12 is advanced into and through the tissue layers until the tip electrode 42 reaches a ventricular pacing site. Advancement of the fixation member 120 into the tissue by rotation of pacemaker 10 may produce the only longitudinal force needed to advance dart electrode 12 through the tissue layers into the ventricular myocardium. In other cases, additional longitudinal force applied at housing proximal end 34 may be required to fully advance dart electrode 12 to its final position.

Figure 12B:
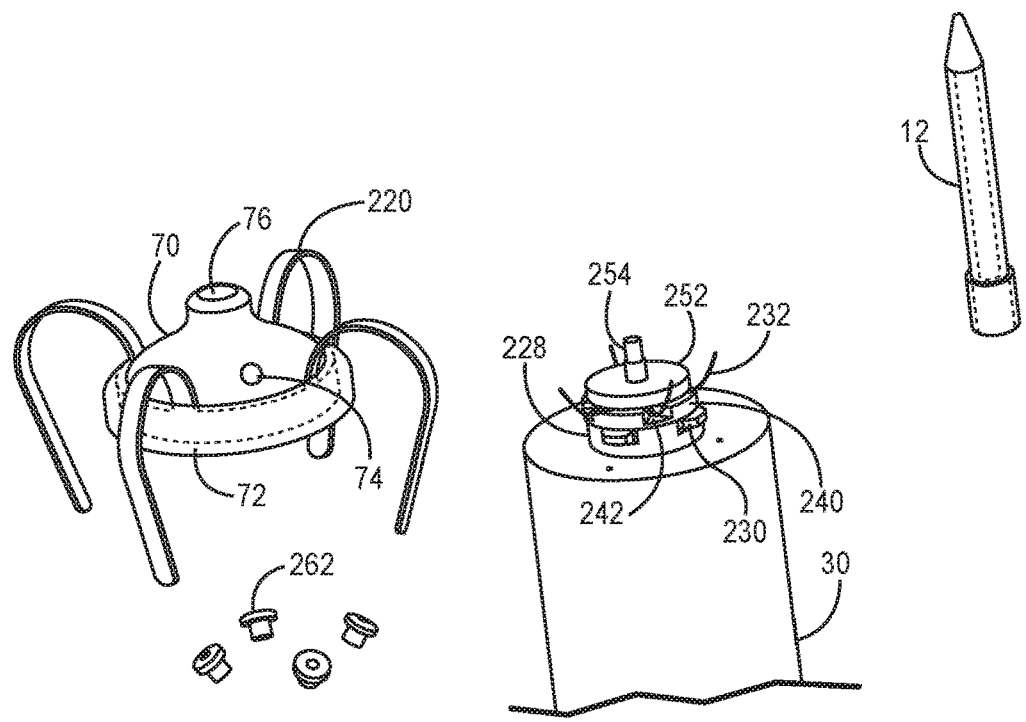
Figure 12C:
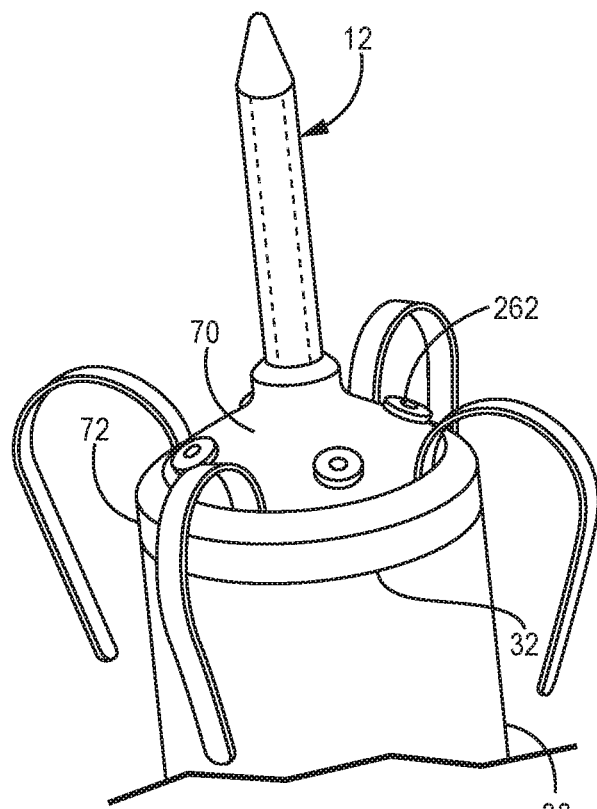

FIGS. 12A-12C are conceptual diagrams of components and a method of assembling distal fixation member and electrode assembly 36 and coupling the assembly 36 to housing 30. FIG. 12A is an exploded view of distal fixation member and electrode assembly 36 according to one example. Assembly 36 may include an inner body 70 and outer ring 72, which may be molded interlocking components shown assembled together in FIG. 12A. Fixation member 220 includes one or more tines 220a, 220b, 220c, and 220d extending from a fixation member ring 224 that may be captured and retained between the inner body 70 and outer ring 72.

Insulated, electrically conductive feedthrough wires 232 and 250 extend from within housing 30 out through an electrical feedthrough 50 extending through distal end cap 228 of housing 30. Feedthrough wires 232 provide electrical connection between circuitry internal to housing 30 to each one of the distal housing-based electrodes 262, which comprises four button electrodes 262a, 262b, 262c, and 262d in this example. Feedthrough wire 250 provides electrical connection from the internal circuitry to tip electrode 42. Distal end cap 228 includes spaced apart, radially-outward extending tabs 230, for interlocking with radially-inward extending tabs 73 of inner body 70 (as best seen in FIG. 6).

A manifold 240 may be provided having radially-extending, horizontal channels 242 for guiding each one of the multiple feedthrough wires 232 to a respective button electrode 262a-d and a central lumen 244 for passing feedthrough wire 250 for electrical coupling to the electrical conductor 46 (shown in FIG. 6) of dart electrode 12. A shaft mounting member 252 may be provided for mechanically coupling and supporting the shaft 40 of dart electrode 12. In some examples, shaft mounting member 252 may provide electrical coupling between feedthrough wire 250 and the electrical conductor 46 (see FIG. 6) within shaft 40 and provides mechanical support of the electrical connection.

Dart electrode 12 may be provided as a subassembly having tip electrode 42 mounted at the distal end of shaft 40 (as described above in conjunction with FIG. 6) and electrically coupled to an electrical conductor 46 extending through shaft 40 to facilitate electrical connection of tip electrode 42 to feedthrough wire 250. Shaft 40 may include a rigid tubular body or a semi-rigid tubular body that is pre-molded or overmolded to enclose the electrical conductor 46 within as described above. Shaft 40 may be non-compressive longitudinally to withstand compressive forces along the longitudinal central axis of dart electrode 12 during insertion of dart electrode 12 into cardiac tissue and advancement of tip electrode 42 to a ventricular pacing site. Shaft 40 may possess lateral flexibility by being elastically deformable in lateral directions. Shaft 40 may be provided with a proximal base 49 configured to seal and reinforce the connection between shaft 40 and shaft mounting member 252.

FIG. 12B is a conceptual diagram of the partially-assembled distal fixation member and electrode assembly 36. Manifold 240 is mounted on distal end cap 228 of housing 30 with feedthrough wires 232 and 250 threaded through manifold 240. Medical adhesive may be applied over the electrical feedthrough 50 to fixedly couple and seal manifold 240 in place over the feedthrough 50 and on distal end cap 228. Shaft mounting member 252 is mounted on top of manifold 240. Shaft-receiving pin 254 may be aligned with the central longitudinal axis of housing 30. Shaft-receiving pin 254 is configured to mate with the proximal end of shaft 40 and may guide a feedthrough wire 250 through a central lumen of pin 254 for electrical coupling to the electrical conductor 46 (shown in FIG. 6) extending within shaft 40. In some examples, feedthrough wire 250 is electrically coupled to shaft-receiving pin 254, and shaft receiving pin 254 is electrically coupled to electrical conductor 46.

In some examples, base 49 is a slidable member that may be advanced distally over shaft 40 during assembly of dart electrode 12 onto shaft-receiving pin 254. Base 49 may be slid down over the junction between shaft receiving pin 254 and shaft 40 to seal, insulate and mechanically reinforce the connections between shaft receiving pin 254, feedthrough wire 250 and the electrical conductor 46 extending within shaft 40. In various examples, welding, adhesive bonding or other bonding methods appropriate for the particular material of shaft mounting member 252 and shaft base 49 may be used to fixedly couple the base 49 of dart electrode 12 to the shaft mounting member 252.

The outer ring 72 and inner body 70 may be sealed together with medical adhesive to form a subassembly including the fixation member 220 retained between outer ring 72 and inner body 70. Inner body 70 of assembly 36 defines a central lumen 76 for passing over dart electrode 12 after it is assembled onto shaft mounting member 252. Inner body 70 further defines electrode cavities 74 for receiving and retaining button electrodes 262a-d. Each of the feedthrough wires 232 corresponding to each of button electrodes 262a-d may be directed toward the respective electrode cavities 74 by manifold 240 to facilitate electrical coupling to respective electrodes 262a-d. After passing inner body 70 over dart electrode 12, each of the remaining feedthrough wires 232 corresponding to distal housing-based electrodes 262a-d are passed through an electrode receiving cavity 74 to enable electrical coupling of each feedthrough wire 232 to a respective one of distal housing-based button electrodes 262a-262d.

FIG. 12C is a conceptual diagram of the completed assembly of distal fixation member and electrode assembly 36. Inner body 70 and outer ring 72 may be aligned with housing 30 to pass over radially-outward extending tabs 230 then rotated to lock radially-inward extending tabs 73 (shown in FIG. 6) in place beneath radially-outward extending tabs 230, with inner body 70 seated over shaft mounting member 252. In other examples, inner body 70 and/or outer ring 72 may include a groove, thread, flange or other feature or combination of features that mate with corresponding features included on distal end cap 228 for aligning and fixedly coupling distal fixation member and assembly 36 with housing 30.

Electrodes 262 may be press fit and sealed or welded into place within respective cavities 74. Trimming (as needed) and spot welding of feedthrough wires 232 to each respective electrode 262 is performed. Medical adhesive, such as silicone adhesive, or other bonding and sealing materials may be applied at joints between dart electrode 12, inner body 70, distal housing-based electrodes 262, outer ring 72 and housing 30 as needed to fixedly couple components of distal fixation member and electrode assembly 36 and housing 30 and promote hermetic sealing and electrical insulation of electrically conductive components from body tissue and fluids (other than intentionally exposed electrode surfaces).

Figure 13:
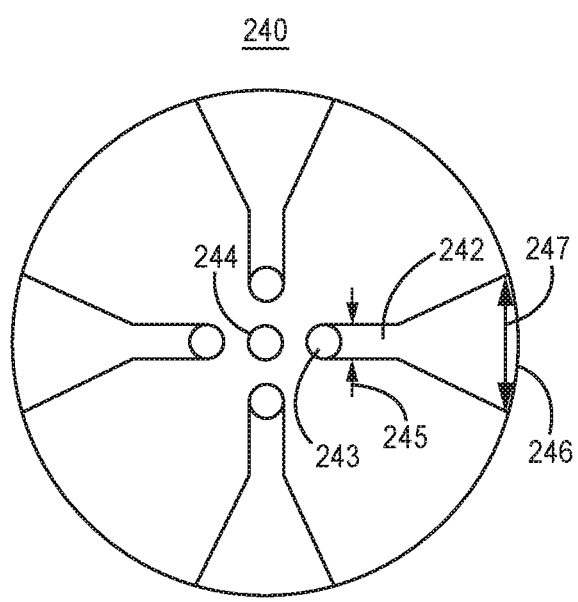
FIG. 13 is a top view of a manifold included in a distal fixation member and electrode assembly according to one example.

FIG. 13 is a top view of manifold 240. Manifold 240 includes a central lumen 244 extending from the bottom surface to the top surface of manifold 240 to pass the feedthrough wire 250 that is electrically coupled to dart electrode 12. In the case of a second electrode carried by the shaft 40 of dart electrode 12, e.g., as shown in FIG. 8, more than one central lumen may be provided or central lumen 244 may accommodate more than one insulated feedthrough wire.

Manifold 240 includes one or more peripheral lumens 243 extending from the bottom surface to the top surface of manifold 240 for passing feedthrough wires 232 to each respective distal housing-based electrode 262. Each peripheral lumen 243 communicates with a horizontal, radially-extending channel 242 for guiding a respective feedthrough wire 232 toward an electrical connection point with a respective housing based electrode 262, e.g., toward a respective electrode cavity 74 of inner body 70. Each channel 242 is shown to have a width that widens moving toward the outer circumference 246 of manifold 240. The width 245 of channel 242 near lumen 243 is less than the width 247 near outer circumference 246. The widening channel width moving toward the outer circumference 246 allows feedthrough wire(s) 232 to shift laterally within the distal fixation member and electrode assembly 36.

For example, feedthrough wires 232 may be threaded through electrode cavities 74 of inner body 70 during the assembly process described above. Inner body 70 assembled with outer ring 72 and fixation member 220 is advanced over dart electrode 12 and seated on distal end cap 228 then rotated to mechanically lock distal fixation member and electrode assembly 36 in place as described in conjunction with FIG. 6. During rotation of inner body 70 and outer ring 72 relative to manifold 240 and housing 30, lateral shifting of feedthrough wires 232 is accommodated by widening channels 242. The gradual widening of channels 242 moving toward outer circumference 246 avoids sharp bends or kinks in the feedthrough wires 232 that may otherwise be caused during the rotation.

Figure 14:
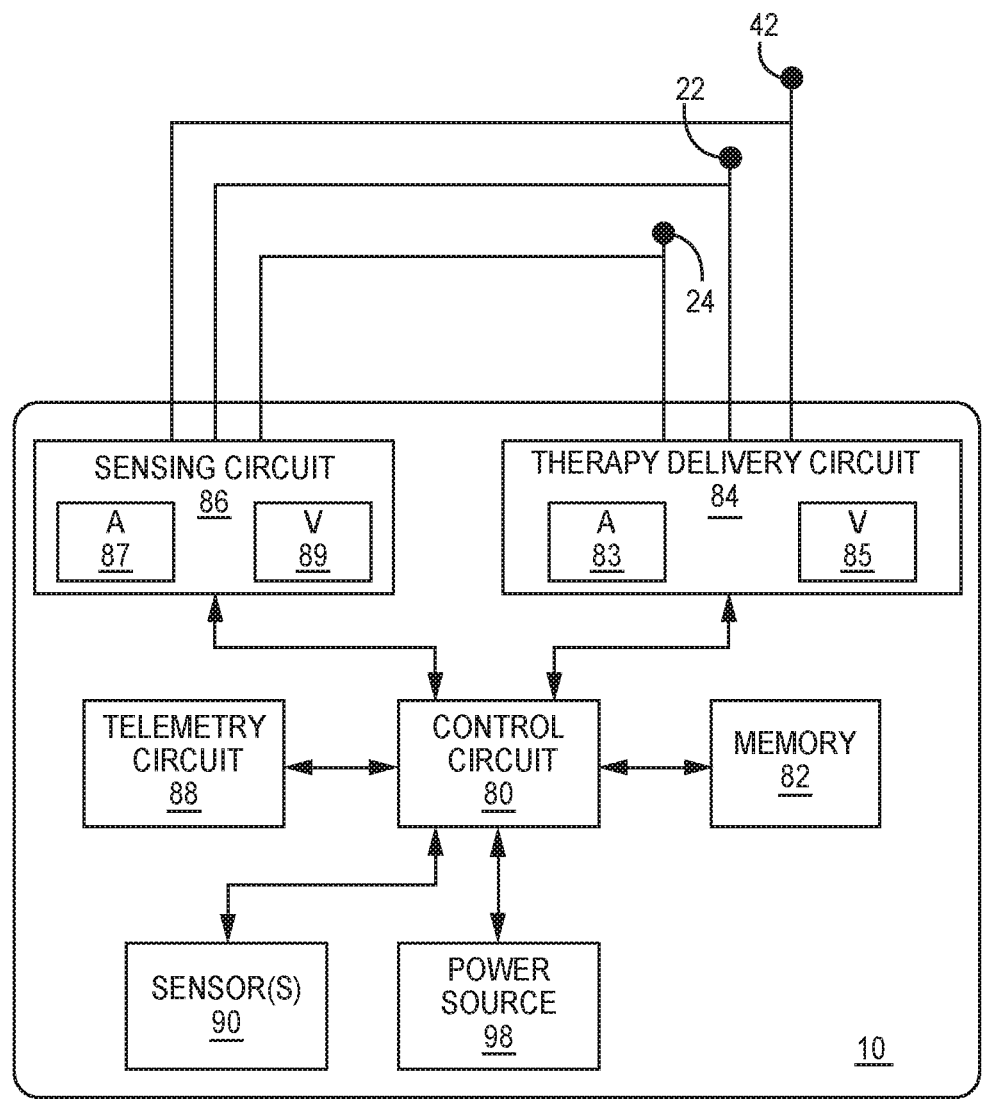
FIG. 14 is a block diagram of circuitry that may be enclosed within the intracardiac pacemaker housing to provide the functions of dual chamber pacing and sensing according to one example.

FIG. 14 is a block diagram of circuitry that may be enclosed within housing 30 to provide the functions of dual chamber pacing and sensing of pacemaker 10 according to one example. The electronic circuitry enclosed within housing 30 includes software, firmware and hardware that cooperatively monitor atrial and ventricular electrical cardiac signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, and telemetry circuit 88. In some examples, pacemaker 10 includes one or more sensors 90 for producing a signal that is correlated to a physiological function, state or condition of the patient, such as a patient activity sensor, for use in determining a need for pacing therapy and/or controlling a pacing rate.

A power source 98 provides power to the circuitry of pacemaker 10 including each of the components 80, 82, 84, 86, 88 and 90 as needed. Power source 98 may include one or more energy storage devices, such as one or more rechargeable or non-rechargeable batteries. The connections between power source 98 and each of the other components 80, 82, 84, 86, 88 and 90 are to be understood from the general block diagram of FIG. 14, but are not shown for the sake of clarity. For example, power source 98 is coupled to one or more charging circuits included in therapy delivery circuit 84 for providing the power needed to charge holding capacitors included in therapy delivery circuit 84 that are discharged at appropriate times under the control of control circuit 80 for delivering pacing pulses, e.g., according to a dual chamber pacing mode such as DDI(R). Power source 98 is also coupled to components of sensing circuit 86, such as sense amplifiers, analog-to-digital converters, switching circuitry, etc., sensors 90, telemetry circuit 88 and memory 82 to provide power to the various circuits as needed.

The functional blocks shown in FIG. 14 represent functionality included in pacemaker 10 and may include any discrete and/or integrated electronic circuit components that implement analog and/or digital circuits capable of producing the functions attributed to dual chamber intracardiac pacemaker 10 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the pacemaker and by the particular detection and therapy delivery methodologies employed by the pacemaker. Providing software, hardware, and/or firmware to accomplish the described functionality in the context of any modern cardiac medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other circuits to perform dual chamber pacing function or other sensing and therapy delivery functions attributed to pacemaker 10. The non-transitory computer-readable media storing the instructions may include any of the media listed above.

Control circuit 80 communicates, e.g., via a data bus, with therapy delivery circuit 84 and sensing circuit 86 for sensing cardiac electrical signals and controlling delivery of cardiac electrical stimulation therapies in response to sensed cardiac events, e.g., P-waves and R-waves, or the absence thereof. Tip electrode 42, distal housing-based electrode 22 (or 52, 62, or 262 as shown FIGS. 4, 5 and 12A-C, respectively), and proximal housing-based electrode 24 are electrically coupled to therapy delivery circuit 84 for delivering electrical stimulation pulses to the patient's heart and to sensing circuit 86 and for sensing cardiac electrical signals.

Sensing circuit 86 includes an atrial (A) sensing channel 87 and a ventricular (V) sensing channel 89. Distal housing-based electrode 22 and proximal housing-based electrode 24 may be coupled to atrial sensing channel 87 for sensing atrial signals, e.g., P-waves attendant to the depolarization of the atrial myocardium. In examples that include two or more selectable distal housing-based electrodes, e.g., electrodes 62a-c in FIG. 5 or electrodes 262a-d in FIG. 12c, sensing circuit 86 may include switching circuitry for selectively coupling one or more of the available distal housing-based electrodes to cardiac event detection circuitry included in atrial sensing channel 87. Switching circuitry may include a switch array, switch matrix, multiplexer, or any other type of switching device suitable to selectively couple components of sensing circuit 86 to selected electrodes. Tip electrode 42 and proximal housing-based electrode 24 may be coupled to ventricular sensing channel 89 for sensing ventricular signals, e.g., R-waves attendant to the depolarization of the ventricular myocardium.

Each of atrial sensing channel 87 and ventricular sensing channel 89 include cardiac event detection circuitry for detecting P-waves and R-waves, respectively, from the cardiac electrical signals received by the respective sensing channels. The cardiac event detection circuitry included in each channel 87 and 89 may be configured to amplify, filter, digitize and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers or other analog or digital components. A cardiac event sensing threshold, e.g., a P-wave sensing threshold and an R-wave sensing threshold, may be automatically adjusted by each respective sensing channel 87 and 89 under the control of control circuit 80, e.g., based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing, sensing circuit 86 may produce a sensed event signal that is passed to control circuit 80. For example, atrial sensing channel 87 may produce a P-wave sensed event signal in response to a P-wave sensing threshold crossing. Ventricular sensing channel 89 may produce an R-wave sensed event signal in response to an R-wave sensing threshold crossing. The sensed event signals are used by control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from atrial sensing channel 87 may cause control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse is inhibited. If the AV pacing interval expires before control circuit 80 receives an R-wave sensed event signal from ventricular sensing channel 89, control circuit 80 controls therapy delivery circuit 84 to deliver the scheduled ventricular pacing pulse synchronized to the sensed P-wave.

In some examples, pacemaker 10 may be configured to deliver a variety of pacing therapies including bradycardia pacing, cardiac resynchronization therapy, post-shock pacing, and/or anti-tachycardia pacing. For example, pacemaker 10 may be configured to detect non-sinus tachycardia and deliver ATP. Control circuit 80 may determine cardiac event time intervals, e.g., PP intervals between consecutive P-wave sensed event signals received from atrial sensing channel 87, RR intervals between consecutive R-wave sensed event signals received from ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

Therapy delivery circuit 84 includes an atrial pacing circuit 83 and a ventricular pacing circuit 85. Each pacing circuit 83 and 85 includes charging circuitry, one or more charge storage devices such as one or more low voltage holding capacitors, an output capacitor, and switching circuitry that controls when the holding capacitor(s) are charged and discharged across the output capacitor to deliver a pacing pulse to the pacing electrode vector coupled to the respective pacing circuit 83 or 85. Tip electrode 42 and proximal housing-based electrode 24 may be coupled to ventricular pacing circuit 85 as a bipolar cathode and anode pair for delivering ventricular pacing pulses, e.g., upon expiration of an AV or VV pacing interval set by control circuit 80 for providing atrial-synchronized ventricular pacing and a basic lower ventricular pacing rate.

Atrial pacing circuit 83 may be coupled to distal housing-based electrode 22 and proximal housing based electrode 24 to deliver atrial pacing pulses. Control circuit 80 may set atrial pacing intervals according to a programmed lower pacing rate or a temporary lower rate set according to a rate-responsive sensor indicated pacing rate. Atrial pacing circuit is controlled to deliver an atrial pacing pulse if the atrial pacing interval expires before a P-wave sensed event signal is received from atrial sensing channel 87. Control circuit 80 starts an AV pacing interval in response to a delivered atrial pacing pulse to provide synchronized dual chamber pacing.

Charging of a holding capacitor of atrial or ventricular pacing circuit 83 or 85 to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes or anti-tachycardia pacing sequences. The microprocessor of control circuit 80 may also set the amplitude, pulse width, polarity or other characteristics of the cardiac pacing pulses, which may be based on programmed values stored in memory 82.

Pacemaker 10 may include other sensors 90 for sensing signals from the patient for use in determining a need for and/or controlling electrical stimulation therapies delivered by therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by control circuit 80 for use in determining a sensor-indicated pacing rate.

Control parameters utilized by control circuit 80 for sensing cardiac events, and controlling pacing therapy delivery may be programmed into memory 82 via telemetry circuit 88. Telemetry circuit 88 includes a transceiver and antenna for communicating with an external device such as a programmer or home monitor, using radio frequency communication or other communication protocols. Under the control of control circuit 80, telemetry circuit 88 may receive downlink telemetry from and send uplink telemetry to the external device. In some cases, telemetry circuit 88 may be used to transmit and receive communication signals to/from another medical device implanted in the patient.

Figure 15:
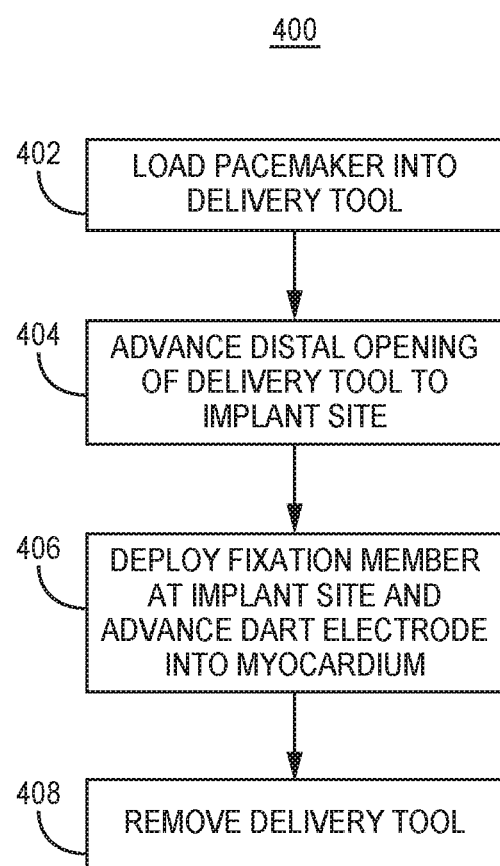
FIG. 15 is a flow chart of a method for using the dual chamber intracardiac pacemaker of FIG. 1.

FIG. 15 is a flow chart of a method for using the dual chamber intracardiac pacemaker 10. At block 402, the intracardiac pacemaker 10 is mounted in a receptacle of a delivery tool, e.g., delivery tool 100 shown in FIG. 9. As shown in FIG. 9, the fixation member 20 may be held in an extended position within the receptacle. At block 404, the distal opening 110 of the delivery tool 100 is advanced to a desired implant site, e.g., the target implant region 4 shown in FIG. 1. At the desired implant site, the fixation member is deployed by advancing the pacemaker 10 out of the distal opening 110 of delivery tool 100, e.g., by an advancement tool 104. As the fixation member is deployed at block 406, the dart electrode 12 is advanced into the cardiac tissue. As described above, the distal tip(s) of the fixation member and the distal tip of the dart electrode may enter the cardiac tissue simultaneously, the dart electrode tip may enter first followed by the fixation member, or the fixation member may enter the tissue first followed by dart electrode 12. If the dart electrode 12 has a greater height than the extended fixation member, the dart electrode 12 may be advanced into the tissue by manual force applied by a clinician along a longitudinal axis of the pacemaker 10 transferred along the center longitudinal axis of shaft 40.

Deployment of the fixation member at block 406 produces a pulling force as the fixation member engages the cardiac tissue, e.g., as elastically deformable tines are advanced into the tissue in a non-relaxed extended position and elastically bend or curve back to the normally curved, relaxed position. The pulling force may contribute to the longitudinal axial force that causes advancement of the tip of the dart electrode into the cardiac tissue, e.g., the myocardium of an adjacent cardiac chamber which may be the ventricular myocardium when housing 30 is located in an atrial chamber. As shown in FIG. 1, the tip electrode of the dart electrode may be advanced into the ventricular septum below the AV node and His bundle. After releasing the pacemaker 10 from the receptacle, the delivery tool is removed from the patient at block 408. Pacemaker housing 30 remains wholly within one heart chamber, e.g., the right atrium, with dart electrode 12 extending into the myocardial tissue of a different heart chamber, e.g., the ventricular septum, to provide pacing and sensing at two different sites, e.g., dual chamber, atrial-synchronized ventricular pacing.

Figure 16:
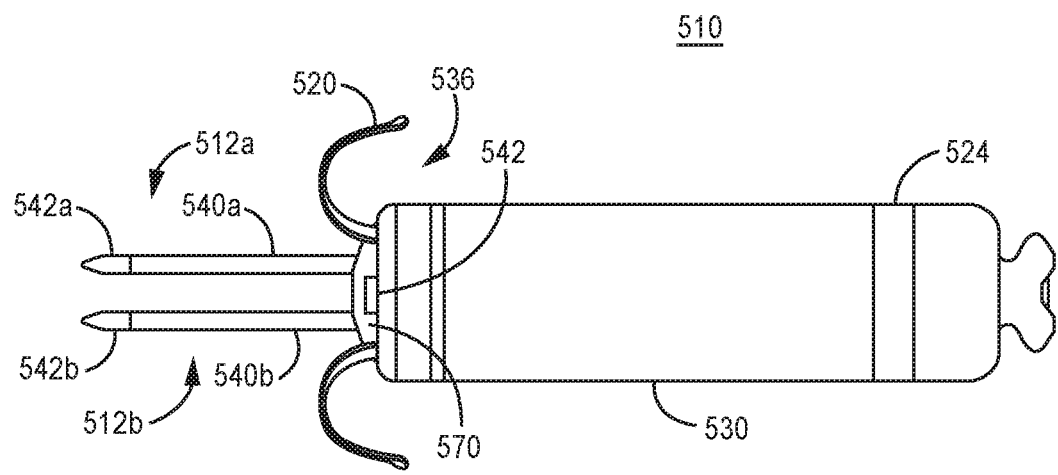
FIG. 16 is a conceptual diagram of an intracardiac pacemaker having more than one distal dart electrode.

FIG. 16 is a conceptual diagram of an intracardiac pacemaker 510 having more than one dart electrode. Pacemaker 510 includes a housing 530 and may include at least one housing based electrode 524 as described in other examples presented herein. The distal fixation and electrode assembly 536 includes fixation member 520, which may include one or more elastically deformable tines as described above. In other examples, the fixation member of pacemaker 510 may include one or more helical tissue engaging portions extending along a peripheral path as shown in FIG. 11.

Distal fixation and electrode assembly 536 may include multiple dart electrodes. Two dart electrodes 512*a* and 512*b* are shown in the example of FIG. 16, extending from inner body 570. Each dart electrode 512*a* and 512*b* includes a straight shaft 540*a* or 540*b* extending distally from inner body 70 each having a respective distal tip electrode 542*a* and 542*b*. In some examples, distal tip electrodes 542*a* and 542*b* are electrically tied together to function as a dual cathode in polarity with a housing-based electrode, e.g., electrode 524, serving as an anode for pacing and/or sensing. In other examples, the tip electrodes 542*a* and 542*b* are each coupled to a separate, insulated conductor and may be selectable one at a time as a single cathode or in combination as a dual cathode. In still other examples, one of electrodes 542*a* or 542*b* may be a cathode electrode and the other of electrodes 542*a* and 542*b* may be an anode to provide bipolar pacing and/or sensing at the tissue depth within which tip electrodes 542*a* and 542*b* are implanted.

Each shaft 540*a* and 540*b* may include an electrical conductor extending within a tubular body from the respective tip electrode 542*a* and 542*b* to a corresponding shaft receiving pin and/or electrical feedthrough wire that electrically couples the tip electrode 542*a* or 542*b* to the pacing and/or sensing circuitry enclosed by housing 530. As described above, each dart electrode 512*a* and 512*b* possesses compressive strength to resist bending or flexing as tip electrodes 542*a* and 542*b* are advanced into cardiac tissue. Each shaft 540*a* and 540*b* may possess lateral flexibility to allow flexion with heart motion in response to lateral forces. While shafts 540*a* and 540*b* are shown having the same length, it is contemplated that when two or more dart electrodes extend from distal fixation and electrode assembly 536, the length and/or diameter of the shafts 540*a* and 540*b* and/or the size and shape of the corresponding tip electrodes 542 and 542*b* may be the same or different.

Pacemaker 510 may be a dual chamber intracardiac pacemaker having tip electrodes 542*a* and 542*b* serving as a cathode and anode pair for sensing and/or pacing in ventricular tissue and a distal housing-based cathode 552 paired with proximal housing-based anode 524 for pacing and sensing in the atrial chamber. In this example, housing-based cathode 552 may include one or more button electrodes or a ring electrode carried distal fixation and electrode assembly 536, as generally described above.

Figure 17:
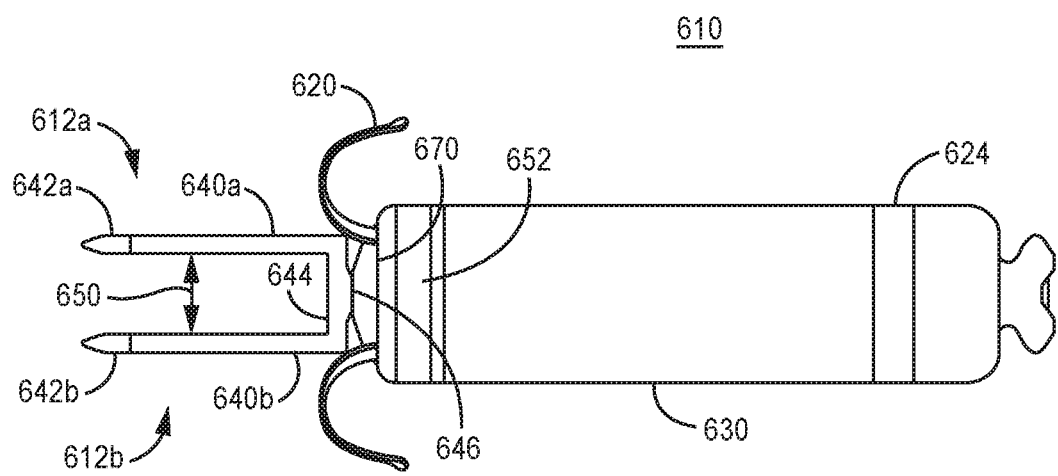
FIG. 17 is a conceptual diagram of an intracardiac pacemaker having more than one distal dart electrode according to another example.

FIG. 17 is a conceptual diagram of an intracardiac pacemaker 610 having more than one distal dart electrode 612*a* and 612*b* according to another example. In this example, the two dart electrodes 612*a* and 612*b* extend from a separator 644 which may extend laterally, e.g., approximately orthogonal to the longitudinal axis of pacemaker 610. Separator 644 may provide a greater separation distance between tip electrodes 642*a* and 642*b* than the separation distance between dart electrodes 512*a* and 512*b* that extend straight out from the inner body 570 of distal fixation and electrode assembly 536. The separation distance of tip electrodes 542*a* and 542*b* carried by dart electrodes 512*a* and 512*b* may be limited by the overall diameter of the distal fixation and electrode assembly 536 when dart electrodes 512*a* and 512*b* each extend straight out from an opening defined by the inner body 570 of assembly 536. Separator 644 may extend outward from a central base 646 that couples the separator 644 (and associated electrical conductors extending there through) to the housing 630.

The shafts 640*a* and 640*b* may each be straight, linear shafts separated by a distance 650 (corresponding to the length of separator 644) that may be equal to or greater than the diameter of inner body 670 or even equal to or greater than the diameter of pacemaker housing 630. In this example, shaft 640*b* is shown having a shorter length than shaft 640*a*, though both shafts may have the same length in other examples. Pacemaker 610 may be a dual chamber intracardiac pacemaker having electrodes 642*a* and 642*b* serving as a cathode and anode pair for sensing and/or pacing in ventricular tissue and a distal housing-based cathode 652, shown as a ring electrode circumscribing distal fixation and electrode assembly 636, paired with proximal housing-based anode 624 for pacing and sensing in the atrial chamber when fixation member 620 anchors housing 630 in an atrial chamber. As such, in various embodiments, an intracardiac pacemaker may include one or more dart electrodes extending from a distal end of the pacemaker to provide one or more tip electrodes positioned at a pacing or sensing site within the cardiac tissue, e.g., in the myocardium of a heart chamber that is adjacent to the heart chamber in which the pacemaker housing is implanted.

Figure 18:
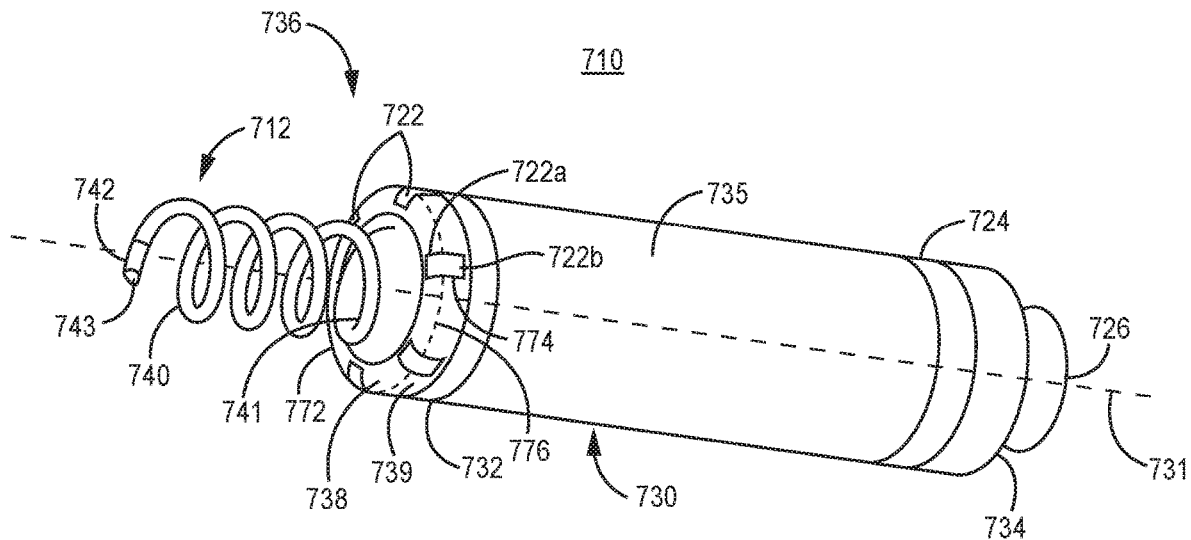
FIG. 18 is a three dimensional perspective view of an intracardiac pacemaker configured for dual chamber cardiac pacing according to yet another example.

FIG. 18 is a three dimensional perspective view of a leadless intracardiac pacemaker 710 configured for dual chamber cardiac pacing according to yet another example. Pacemaker 710 includes a housing 730 having an outer sidewall 735, shown as a cylindrical outer sidewall, extending from a housing distal end 732 to a housing proximal end 734. Housing 730 encloses electronic circuitry configured to perform atrial and ventricular cardiac electrical signal sensing and for delivering dual chamber pacing to the atrial and ventricular chambers as needed, e.g., as described above in conjunction with FIG. 14. A delivery tool interface member 726 is shown on the housing proximal end 734.

A distal fixation and electrode assembly 736 is coupled to the housing distal end 732. Distal fixation and electrode assembly 736 may include an electrically insulative distal member 772 coupled to housing distal end 732. A tissue piercing electrode 712 extends away from housing distal end 732, and multiple non-tissue piercing electrodes 722 are coupled directly to insulative distal member 772. The tissue piercing electrode 712 extends in a longitudinal direction away from housing distal end 732 and may be coaxial with the longitudinal center axis 731 of housing 730.

Tissue piercing distal electrode 712 includes an electrically insulated shaft 740 and a tip electrode 742. In some examples, tissue piercing distal electrode 712 is an active fixation member including a helical shaft 740 and a distal cathode tip electrode 742. The helical shaft 740 extends from a shaft distal end 743 to a shaft proximal end 741 that is directly coupled to insulative distal member 772. Helical shaft 740 may be coated with an electrically insulating material, e.g., parylene or other examples listed herein, to avoid sensing or stimulation of cardiac tissue along the shaft length. Tip electrode 742 is at the shaft distal end 743 and may serve as a cathode electrode for delivering ventricular pacing pulses and sensing ventricular electrical signals using proximal housing based electrode 724 as a return anode when the tip electrode 742 is advanced into ventricular tissue. Proximal housing based electrode 724 may be a ring electrode circumscribing housing 730 and may be defined by an uninsulated portion of longitudinal sidewall 724. Other portions of housing 730 not serving as an electrode may be coated with an electrically insulating material as described above in conjunction with FIG. 2.

Multiple non-tissue piercing electrodes 722 are provided along a periphery of insulative distal member 772, peripheral to tissue piercing electrode 712. Insulative distal member 772 defines a distal-facing surface 738 of pacemaker 710 and a circumferential surface 739 that circumscribes pacemaker 710 adjacent to housing longitudinal sidewall 735. Non-tissue piercing electrodes 722 may be formed of an electrically conductive material, such as titanium, platinum, iridium or alloys thereof. In FIG. 18, six non-tissue piercing electrodes 722 are spaced apart radially at equal distances along the outer periphery of insulative distal member 772, however two or more non-tissue piercing electrodes 722 may be provided.

Non-tissue piercing electrodes 722 may be discrete components each retained within a respective recess 774 in insulative member 772 that is sized and shaped to mate with a non-tissue piercing electrode 722. In other examples, non-tissue piercing electrodes 722 may each be an uninsulated, exposed portion of a unitary member mounted within or on insulative distal member 772. Intervening portions of the unitary member not functioning as an electrode may be insulated by insulative distal member 772 or, if exposed to the surrounding environment, coated with an electrically insulating coating, e.g., parylene, polyurethane, silicone, epoxy, or other insulating coating.

When tissue piercing electrode 712 is advanced into cardiac tissue, at least one of the non-tissue piercing electrodes 722 is positioned against, in intimate contact with or in operative proximity to, a cardiac tissue surface for delivering pacing pulses and/or sensing cardiac electrical signals produced by the patient's heart. For example, non-tissue piercing electrodes 722 may be positioned in contact with right atrial endocardial tissue for pacing and sensing in the atrium when tissue piercing electrode 712 is advanced into the atrial tissue and through the central fibrous body until distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and sensing circuit 86 enclosed by housing 730 to function collectively as a cathode electrode for delivering atrial pacing pulses and for sensing atrial electrical signals, e.g., P-waves, in combination with the proximal housing-based electrode 724 as a return anode. Switching circuitry included in sensing circuit 86 may be activated under the control of control circuit 80 to couple one or more of the non-tissue piercing electrodes to atrial sensing channel 87. The distal, non-tissue piercing electrodes 722 may be electrically isolated from each other so that each individual one of electrodes 722 may be individually selected by switching circuitry included in therapy delivery circuit 84 to serve alone or in a combination of two or more of electrodes 722 as an atrial cathode electrode. Switching circuitry included in therapy delivery circuit 84 may be activated under the control of control circuit 80 to couple one or more of the non-tissue piercing electrodes 722 to atrial pacing circuit 83. Two or more of the non-tissue piercing electrodes 722 may be selected at a time to operate as a multi-point atrial cathode electrode.

The particular ones of the non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from power source 98.

In some instances, the distal-facing surface 738 may uniformly contact the atrial endocardial surface when tissue piercing electrode 712 anchors the housing 730 at an implant site. In that case, all of electrodes 722 may be selected together to form the atrial cathode. Alternatively, every other one of electrodes 722 may be selected together to form a multi-point atrial cathode having a higher electrical impedance that is still uniformly distributed along the distal-facing surface 738. Alternatively, a subset of one or more electrodes 722 along one side of insulative distal member 772 may be selected to provide pacing at a desired site that achieves the lowest pacing capture threshold due to the relative location of electrodes 722 to the atrial tissue being paced.

In other instances, the distal-facing surface 738 may be oriented at an angle relative to the adjacent endocardial surface depending on the positioning and orientation at which the tissue piercing electrode 712 enters the cardiac tissue. In this situation, one or more of the non-tissue piercing electrodes 722 may be positioned in closer contact with the adjacent endocardial tissue than the other non-tissue piercing electrodes 722, which may be angled away from the endocardial surface. By providing multiple non-tissue piercing electrodes along the periphery of the insulative distal member 772, the angle of tissue piercing electrode 712 and housing distal end 732 relative to the cardiac surface, e.g., the right atrial endocardial surface, is not required to be substantially parallel. Anatomical and positional differences may cause the distal-facing surface 738 to be angled or oblique to the endocardial surface, however, the multiple non-tissue piercing electrodes 722 distributed along the periphery of insulative distal member 772 increase the likelihood of good contact between one or more electrodes 722 and the adjacent cardiac tissue to promote acceptable pacing thresholds and reliable cardiac event sensing using at least a subset of the multiple electrodes 722. Contact or fixation circumferentially along the entire periphery of the insulative distal member 772 is not required.

The non-tissue piercing electrodes 722 are shown to each include a first portion 722a extending along the distal-facing surface 738 and a second portion 722b extending along the circumferential surface 739. The first portion 722a and second portion 722b may be continuous exposed surfaces such that the active electrode surface wraps around the peripheral edge 776 of insulative distal member 772 that joins the distal facing surface 738 and circumferential surface 739. The non-tissue piercing electrodes 722 may include one or more of electrodes 772 along distal-facing surface 738, one or more along circumferential surface 739, one or more electrodes each extending along both of the distal-facing surface 738 and the circumferential surface 739, or any combination thereof. The exposed surface of each of the non-tissue piercing electrodes 722 may be flush with the respective distal-facing surface 738 and/or circumferential surface. In other examples, each of non-tissue piercing electrodes 722 may have a raised surface that protrudes from insulative distal member 772. Any raised surface of electrodes 722, however is a smooth or rounded, non-tissue piercing surface.

Since distal fixation and electrode assembly 736 seals the distal end of housing 730 and provides a foundation on which the electrodes 722 are mounted, the electrodes 722 may be referred to as housing-based electrodes. These electrodes 722 are not carried by a shaft or other extension that extends the active electrode portion away from the housing 730, like distal tip electrode 742 residing at the distal tip of helical shaft 740 extending away from housing 730. Other examples of non-tissue piercing electrodes presented herein that are coupled to a distal-facing surface and/or a circumferential surface of an insulative distal member include distal housing based ring electrode 22 (FIG. 3), distal housing based ring electrode 52 extending circumferentially around assembly 36 (FIG. 4), button electrodes 62a-c (FIG. 5), button electrodes 262 (FIG. 12C), housing based electrode 552 (FIG. 16) and circumferential ring electrode 652 (FIG. 17). Any of these non-tissue piercing electrodes directly coupled to a distal insulative member, peripherally to a central tissue-piercing electrode, may be provided to functioning individually, collectively, or in any combination as a cathode electrode for delivering pacing pulses to adjacent cardiac tissue. When a ring electrode, such as distal ring electrode 22 and/or circumferential ring electrode 52 is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue piercing electrode provided along distal fixation and electrode assembly 736. The atrial chamber walls are relatively thin compared to ventricular chamber walls. A tissue piercing atrial cathode electrode may extend too deep within the atrial tissue leading to inadvertent sustained or intermittent capture of ventricular tissue. A tissue piercing atrial cathode electrode may lead to interference with sensing atrial signals due to ventricular signals having a larger signal strength in the cardiac electrical signal received via tissue-piercing atrial cathode electrodes that are in closer physical proximity to the ventricular tissue. The tissue piercing electrode 712 may be securely anchored into ventricular tissue stabilizing the implant position of pacemaker 710 and providing reasonable certainty that tip electrode 742 is sensing and pacing in ventricular tissue while the non-tissue piercing electrodes 722 are reliably pacing and sensing in the atrium. When pacemaker 710 is implanted in the target implant region 4, e.g., as shown in FIG. 1, the tip electrode 742 may reach left ventricular tissue for pacing of the left ventricle while non-tissue piercing electrodes 722 provide pacing and sensing in the right atrium. Tissue piercing electrode 712 may be in the range of 4 mm to 8 mm in length from distal-facing surface 738 to reach left ventricular tissue. In some instances, pacemaker 710 may achieve four chamber pacing by delivering atrial pacing pulses from atrial pacing circuit 83 via the non-tissue piercing electrodes 722 in the target implant region 4 to achieve bi-atrial (right and left atrial) capture and by delivering ventricular pacing pulses from ventricular pacing circuit 85 via tip electrode 742 advanced into ventricular tissue from target implant region 4 to achieve biventricular (right and left ventricular) capture.

Figure 19:
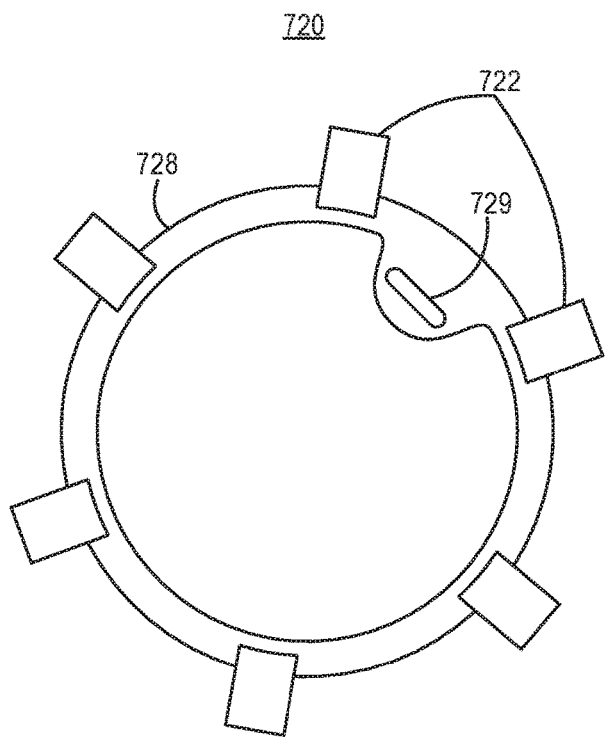
FIG. 19 is a top schematic view of a unitary member including a continuous ring carrying multiple non-tissue piercing electrodes which may be included in the pacemaker of FIG. 18.

FIG. 19 is a top schematic view of a unitary member 720 including a continuous ring 728 along which electrodes 722 are mounted. Unitary member 720 may be a machined component formed from a conductive metal. In other examples, unitary member 720 may be an assembly of multiple parts in which electrodes 722 are mechanically coupled to ring 728, for example by welding or adhesively coupling. Ring 728 may define an aperture 729 through which one or more electrically conductive feedthrough wires may extend for electrically coupling unitary member (and thus all of electrodes 722) to circuitry within pacemaker 710. Aperture 729 is shown as an elongated aperture to allow unitary member 720 and insulative distal member 772 to be rotatably coupled to housing 730 when electrically conductive feedthrough wires extend through aperture 729.

Figure 20:
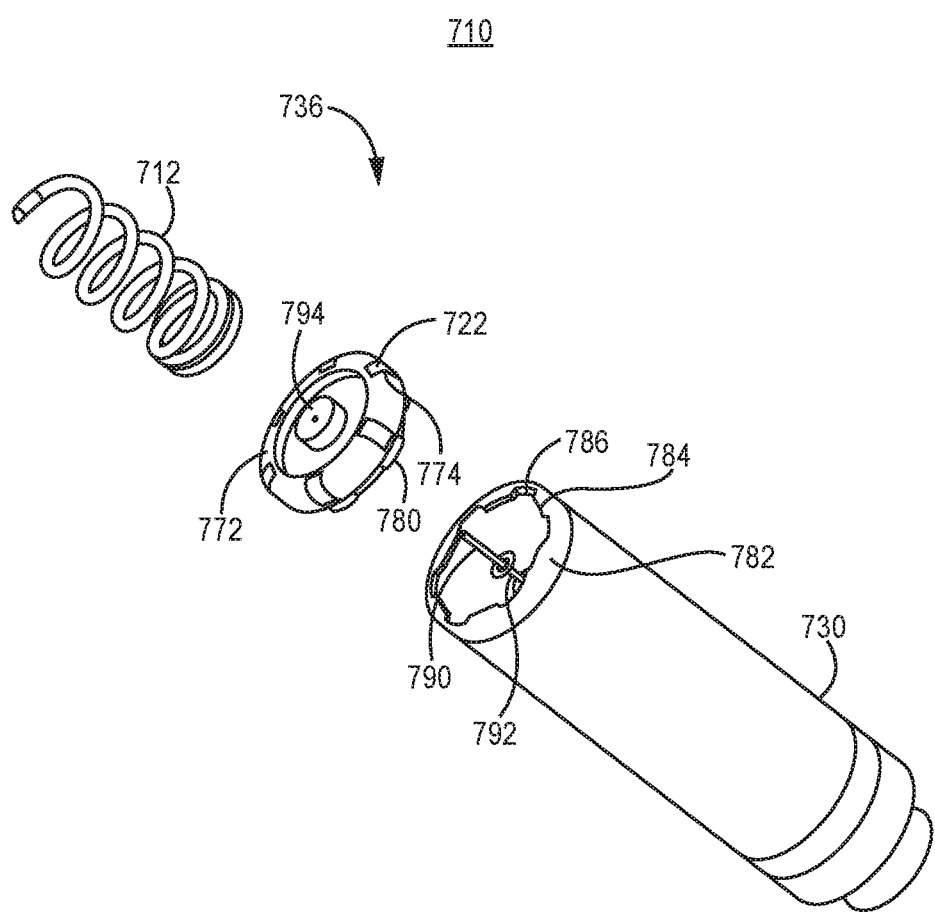
FIG. 20 is a three dimensional, exploded view of the distal fixation and electrode assembly of the pacemaker of FIG. 18.

FIG. 20 is a three dimensional, exploded view of the distal fixation and electrode assembly 736 of pacemaker 710. Insulative distal member 772 may be overmolded onto unitary member 720 such that non-tissue piercing electrodes 722 are exposed at each recess 774. Insulative distal member 772 may include radially-extending tabs 780 for interlocking with retaining tabs 784 of a distal end cap 782 of housing 730. Radially-extending tabs 780 may be aligned with notches 786 of distal end cap 782 to place insulative distal member 772 against distal end cap 782. Insulative distal member 772 may be rotated so that radially-extending tabs 780 are captured beneath retaining tabs 784 of distal end cap 782.

A central feedthrough wire 790 extends through distal end cap 782 and insulative distal member 772 to be electrically coupled to tissue piercing electrode 712, e.g., via an electrically conductive coupler 794. The tissue-piercing electrode 712 may be mounted on coupler 794 such that shank 740 is electrically coupled to feedthrough wire 790 via coupler 794. One or more peripheral feedthrough wires 792 extend through distal end cap 782 and the aperture 729 (FIG. 19) for electrical connection to non-tissue piercing electrodes 722. A single peripheral feedthrough wire 792 may be electrically coupled to a unitary member (e.g., member 720 of FIG. 19) that carries all of and is electrically coupled to electrodes 722. In examples that include individually selectable electrodes, multiple peripheral feedthrough wires extending through a single aperture or multiple apertures may be electrically coupled to respective electrodes 722. After the distal fixation and electrode assembly 736 is assembled onto distal end cap 782 and necessary electrical connections have been made, a medical adhesive may be applied to hermetically seal and protect the electrical connections. The example of FIG. 20 represents one method of assembling multiple non-tissue piercing electrodes peripheral to a central tissue piercing electrode at the distal end of pacemaker housing 730. It is recognized that other assembly methods may be used to provide multiple non-tissue piercing electrodes along the distal-facing surface 738 and/or circumferential surface 739.

Figure 21:
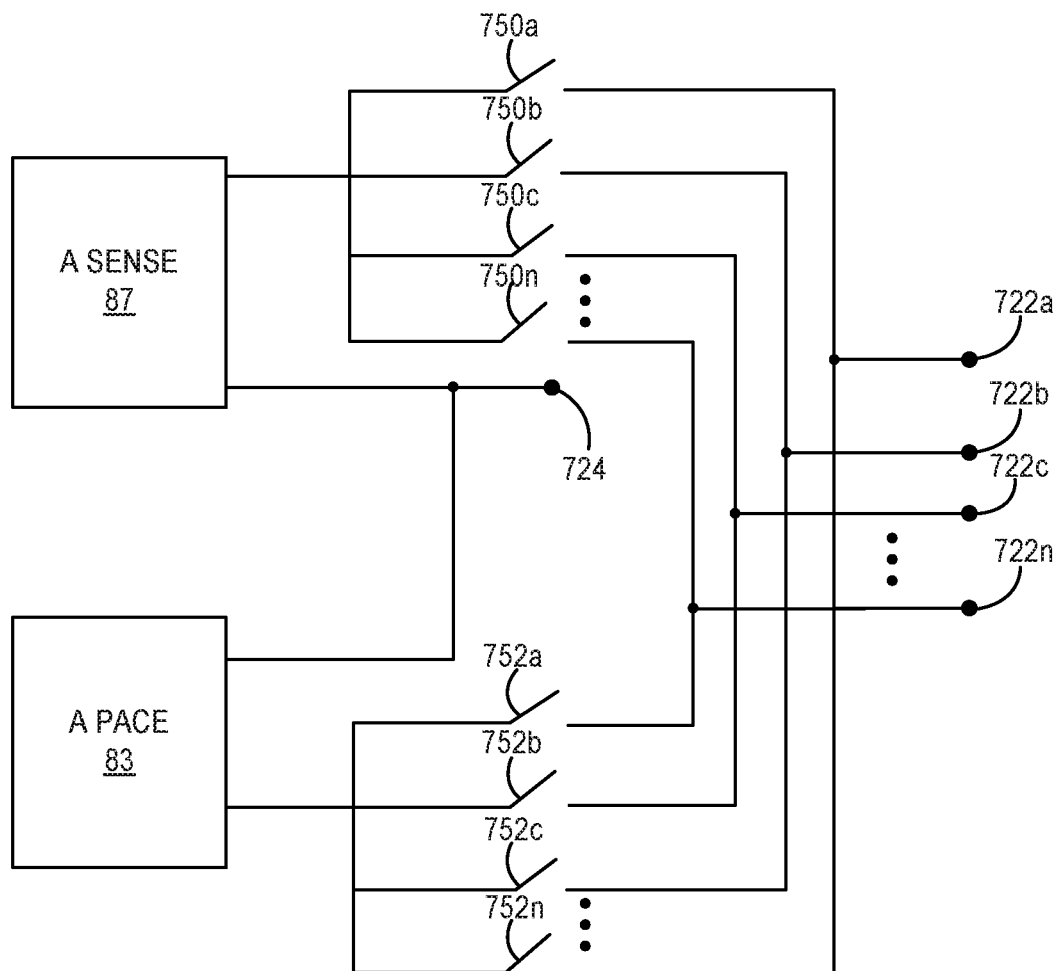
FIG. 21 is a conceptual diagram of an atrial sensing channel and an atrial pacing circuit coupled to the multiple non-tissue piercing cathode electrodes via switching circuitry.

FIG. 21 is a conceptual diagram of the atrial sensing channel 87 of sensing circuit 86 and atrial pacing circuit 83 of therapy delivery circuit 84 (shown in FIG. 14) coupled to the multiple electrodes 722 via switching circuitry 750 and 752. The sensing circuit 86 may include multiple switches 750a-n, collectively 750, that may be controlled by sensing circuit 86 in response to control signals received from control circuit 80. Sensing circuit 86 opens and closes switches 750a-n at appropriate times for electrically coupling respective electrodes 722a-n to atrial sensing channel 87, one or more at a time. One, two, three or more, up to all n electrodes 722a-n, may be switchably coupled to atrial sensing channel 87 at a time to function as a single or multi-point cathode electrode for sensing atrial signals in combination with housing-based anode electrode 724.

Therapy delivery circuit 84 includes multiple switches 752a-n, collectively switches 752, for selectively coupling electrodes 722a-n to atrial pacing circuit 83 in any desired combination. One, two, three or more, up to all n electrodes 722a-n, may be electrically coupled to atrial pacing circuit 83 via switches 752a-n for functioning as a single or multi-point cathode electrode for delivering atrial pacing pulses. Control circuit 80 may be configured to control therapy delivery circuit 84 to select one or a combination of two or more electrodes 722a-n to serve as the atrial pacing cathode.

Electrodes 722a-n may include six non-tissue piercing electrodes peripheral to the tissue piercing electrode 712, as shown in FIG. 18, but may include fewer than six electrodes or more than six electrodes in other examples. In any of the examples presented herein that include multiple, non-tissue piercing electrodes along a distal-facing and/or circumferential surface of the distal fixation and electrode assembly, each of the non-tissue piercing electrodes may be electrically isolated from one another and coupled to electrically isolated conductors that couple each non-tissue piercing electrode to the atrial sensing channel 87 and/or the atrial pacing circuit 83 via the respective switches 750a-n and 752a-n.

Figure 22:
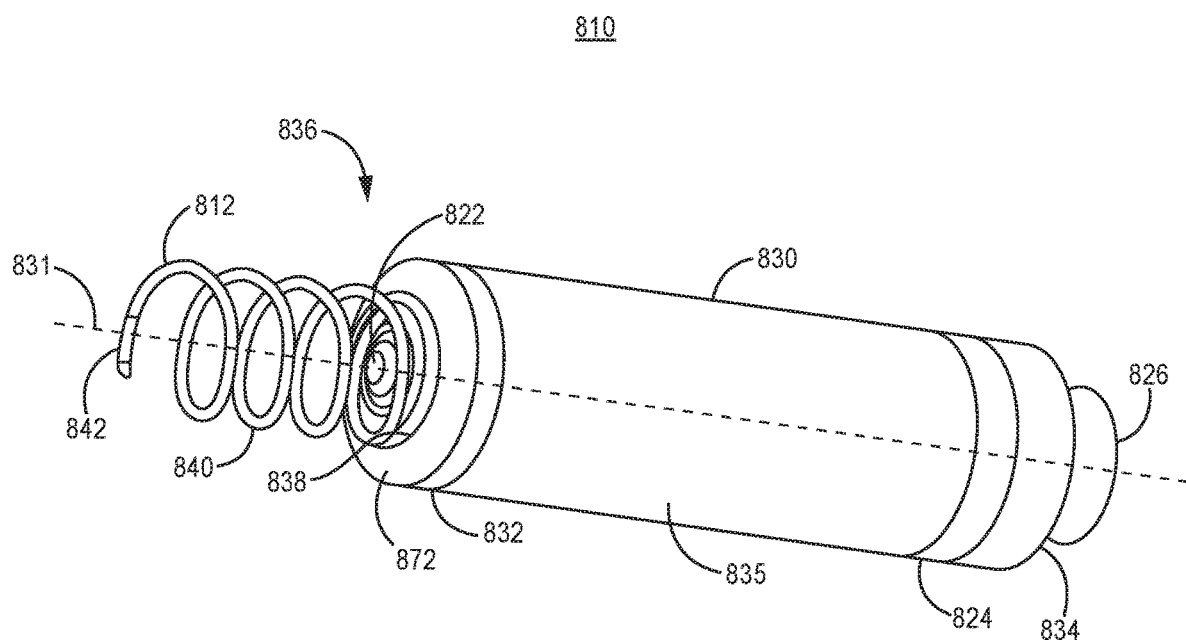
FIG. 22 is a three-dimensional view of a pacemaker according to another example.

FIG. 22 is a three-dimensional view of a pacemaker 810 according to another example. Pacemaker 810 includes a housing 830 having a cylindrical longitudinal sidewall 835 extending from a housing proximal end 834 to a housing distal end 832. A delivery tool interface member 826 may extend from the housing proximal end 834 as described previously herein. A distal fixation and electrode assembly 836 is coupled directly to the housing distal end 832.

Distal fixation and electrode assembly 836 includes an insulative member 872 having a distal-facing surface 838, a tissue piercing distal electrode 812, and a non-tissue piercing distal electrode 822. Tissue piercing distal electrode 812 extends in a longitudinal direction away from housing distal end 832 and may be coaxial with the longitudinal center axis 831 of housing 830. Tissue piercing distal electrode 812 includes an electrically insulated shaft 840 and a tip electrode 842. In this example, tissue piercing distal electrode 812 is an active fixation member including a helical shaft 840 and a distal tip electrode 842 which may function as a cathode electrode for pacing and sensing in a heart chamber adjacent to the chamber in which pacemaker 810 is implanted. For example, when the tip electrode 842 is advanced into ventricular tissue and housing 830 is implanted in the right atrium, tip electrode 842 may serve as a cathode electrode for delivering ventricular pacing pulses and sensing ventricular electrical signals using proximal housing based electrode 824 as a return anode.

Tissue piercing distal electrode 812 is peripheral to non-tissue piercing electrode 822 on distal-facing surface 838. Non-tissue piercing electrode 822 may be, for example, a button or hemispherical electrode that protrudes from a central portion of distal-facing surface 838 and is circumscribed or encircled by, but spaced apart and electrically isolated from, helical shaft 840 of tissue piercing distal electrode 812. In some examples, non-tissue piercing electrode 822 includes a coating or is a steroid eluting electrode. For example, non-tissue piercing electrode 822 may be a ring electrode defining a central opening or may include a recess or concavity for retaining an MCRD including a polymer matrix, e.g., a silicone or polyurethane base, and a steroid, e.g., sodium dexamethasone phosphate, compounded in the polymer matrix for eluting over time to reduce the foreign body response at the implant site. Both non-tissue piercing distal electrode 822 and helical shaft 840 may be centered along the longitudinal center axis of housing 830 in some examples with helical shaft 840 winding around and centered on non-tissue piercing distal electrode 822.

When tissue piercing distal electrode 812 is fully advanced from the right atrium into direct contact with the ventricular myocardial or conductive tissue, the non-tissue piercing distal electrode 822 is anchored against or in operative proximity to atrial tissue. The active fixation of housing 830 in the atrial chamber by tissue piercing distal electrode 812 maintains the position of tip electrode 842 for ventricular sensing and pacing and the position of non-tissue piercing distal electrode 822 for atrial pacing and sensing for providing dual chamber pacing. Non-tissue piercing distal electrode 822 may function as an atrial cathode electrode for pacing the right atrium and sensing atrial signals in combination with proximal housing-based electrode 824 serving as the anode.

Thus, a pacemaker has been presented in the foregoing description with reference to specific embodiments. It is to be understood that various aspects disclosed herein may be combined in different combinations than the specific combinations presented in the accompanying drawings. It is appreciated that various modifications to the referenced embodiments may be made without departing from the scope of the disclosure and the following claims.

What is claimed is:

1. An intracardiac pacemaker comprising:
    an elongated housing having a proximal end and a distal end;
    a pacing circuit enclosed by the elongated housing;
    a dart electrode coupled to the distal end of the elongated housing configured to pierce cardiac tissue, the dart electrode comprising:
       a shaft having a normally straight position extending away from the housing distal end;
       an electrical conductor extending through the shaft; and
       a first electrode carried by the shaft, the first electrode being electrically coupled to the pacing circuit via the electrical conductor, wherein the first electrode is a first cathode electrode;
    a fixation member that extends from the elongated housing at a location that is peripheral from the shaft and configured to fix the elongated housing at an implant site within a heart;
    a housing-based electrode carried by the elongated housing, wherein the housing-based electrode is an anode electrode;
    a second cathode electrode proximal to the first cathode electrode;
    a sensing circuit; and
    a control circuit,
    wherein the pacing circuit is configured to deliver pacing pulses to ventricular myocardium using the first cathode electrode and the housing-based anode electrode and configured to deliver pacing pulses to the atrial myocardium using the second cathode electrode and the housing-based anode electrode,
    wherein the sensing circuit is configured to sense ventricular electrical events from a first cardiac electrical signal received via the first cathode electrode and the housing-based anode electrode and configured to sense atrial electrical events from a second cardiac electrical signal received via the second cathode electrode and the housing-based anode electrode, and
    wherein the control circuit is coupled to the sensing circuit and the pacing circuit and configured to control the pacing circuit to deliver atrial pacing pulses via the second cathode electrode and the housing-based anode electrode and deliver ventricular pacing pulses via the first cathode electrode and the housing based anode electrode.

2. The pacemaker of claim 1, wherein the first electrode comprises a shank residing within the shaft and an exposed electrode portion having a blunt tip that pierces the cardiac tissue.

3. The pacemaker of claim 2, wherein the first electrode has a maximum width that is isodiametric with the shaft.

4. The pacemaker of claim 1, wherein the first electrode comprises a shank residing within the shaft and an exposed electrode portion having a rounded tip that pierces the cardiac tissue.

5. The pacemaker of claim 1, wherein the shaft comprises a tubular body that resists bending in response to a compressive force along a central longitudinal axis of the shaft.

6. The pacemaker of claim 4, wherein the tubular body is an overmolded body that circumscribes the electrical conductor.

7. The pacemaker of claim 1, wherein the dart electrode is a component of a distal assembly, and wherein the distal assembly further comprises the second cathode electrode.

8. The pacemaker of claim 7, wherein the second cathode electrode comprises an electrically conductive surface of the shaft proximal to the first electrode.

9. The pacemaker of claim 7, wherein the distal assembly comprises a distal surface and the second cathode electrode resides along the distal surface.

10. The pacemaker of claim 9, wherein the second cathode electrode comprises a plurality of electrodes distributed along the distal surface.

11. The pacemaker of claim 9, wherein the plurality of electrodes are individually selectable by the pacing circuit.

12. The pacemaker of claim 1, wherein the dart electrode is a component of a distal assembly, wherein the distal assembly comprises the second cathode electrode, wherein the second cathode electrode extends circumferentially around the distal assembly.

13. The pacemaker of claim 1, wherein the dart electrode is at least 3 millimeters long and up to 12 mm long and has a tissue-piercing distal tip with a maximum diameter of 1 millimeter.

14. The pacemaker of claim 1, wherein the dart electrode comprises a steroid eluting member.

15. The pacemaker of claim 1, wherein:
the housing comprises a distal end cap and an electrical feedthrough extending through the distal end cap, the electrical feedthrough comprising a plurality of feed through wires;
the dart electrode is a component of a distal assembly, and wherein the distal assembly further comprises a manifold having a top surface, a bottom surface and an outer circumference, the manifold comprising:
a plurality of lumens extending from the top surface to the bottom surface, each lumen receiving a respective one of the plurality of feedthrough wires;
at least one horizontal channel in communication with a respective one of the plurality of lumens, the horizontal channel extending radially from the respective lumen toward the outer circumference and having a first width at the respective lumen and a second width at the outer circumference, wherein the second width is greater than the first width.

16. The pacemaker of claim 15, wherein:
the distal assembly further comprises a shaft mounting member coupled to the top surface of the manifold, the shaft mounting member comprising a shaft receiving pin,
one of the plurality of feed through wires is electrically coupled to the shaft mounting member, and
the shaft receiving pin extends at least partially into the shaft of the dart electrode and is electrically coupled to the electrical conductor.

17. The pacemaker of claim 16, wherein the dart electrode comprises a shaft base circumscribing an interface between the shaft mounting member and the shaft of the dart electrode.

18. The pacemaker of claim 1, wherein the fixation member comprises a plurality of tines each having a tissue-piercing distal tip, the plurality of tines each elastically deformable to an extended position in which each tine tip is at a first height from the housing distal end, and the first electrode having a distal tip at a second height from the housing distal end different than the first height.

19. The pacemaker of claim 1, wherein:
the pacing circuit comprises a ventricular pacing circuit and an atrial pacing circuit, wherein the first cathode electrode and the housing-based anode electrode are electrically coupled to the ventricular pacing circuit, and wherein the second cathode electrode and the housing-based anode electrode are electrically coupled to the atrial pacing circuit;
the sensing circuit comprises an atrial channel and a ventricular channel, wherein the ventricular channel is configured to sense the ventricular electrical events from the first cardiac electrical signal, and wherein the atrial channel is configured to sense the atrial electrical events from the second cardiac electrical signal; and
the control circuit is configured to control the atrial pacing circuit to deliver atrial pacing pulses via the second cathode electrode and the housing-based anode electrode and configured to control the ventricular pacing circuit to deliver ventricular pacing pulses via the first cathode electrode and the housing based anode.

20. The pacemaker of claim 1, further comprising a second dart electrode comprising a second shaft having a normally straight position and an electrode carried by the second shaft.

21. A pacemaker having a housing enclosing a pacing circuit and comprising:
an assembly coupled to the housing, the assembly comprising:
a dart electrode configured to pierce cardiac tissue at an implant site along a chamber of a patient's heart and comprising:
a shaft having a normally straight position and extending away from the housing,
an electrical conductor extending through the shaft, and
a first electrode carried by the shaft, the first electrode being electrically coupled to the pacing circuit via the electrical conductor, wherein the first electrode is a first cathode electrode;
a fixation member that extends from the assembly at a location that is peripheral from the shaft and configured to fix the assembly at the implant site;
a housing-based electrode carried by the elongated housing, wherein the housing-based electrode is an anode electrode;
a second cathode electrode proximal to the first cathode electrode;
a sensing circuit; and
a control circuit,
wherein the pacing circuit is configured to deliver pacing pulses to ventricular myocardium using the first cathode electrode and the housing-based anode electrode and configured to deliver pacing pulse to the atrial myocardium using the second cathode electrode and the housing-based anode electrode,
wherein the sensing circuit is configured to sense ventricular electrical events from a first cardiac electrical signal received via the first cathode electrode and the housing-based anode electrode and configured to sense atrial electrical events from a second cardiac electrical signal received via the second cathode electrode and the housing-based anode electrode, and
wherein the control circuit is coupled to the sensing circuit and the pacing circuit and configured to control the pacing circuit to deliver atrial pacing pulses via the second cathode electrode and the housing-based anode electrode and deliver ventricular pacing pulses via the first cathode electrode and the housing based anode electrode.

22. The pacemaker of claim 21, wherein the first electrode comprises a shank residing within the shaft and an exposed electrode portion having a blunt tip that pierces the cardiac tissue.

23. The pacemaker of claim 22, wherein the first electrode has a maximum width that is isodiametric with the shaft.

24. The pacemaker of claim 21, wherein the first electrode comprises a shank residing within the shaft and an exposed electrode portion having a rounded tip that pierces the cardiac tissue.

25. The pacemaker of claim 21, wherein the shaft comprises a tubular body that resists bending in response to a compressive force along a central longitudinal axis of the shaft.

26. The pacemaker of claim 25, wherein the tubular body is an overmolded body that circumscribes the electrical conductor.

27. The pacemaker of claim 21, wherein the assembly comprises the second cathode electrode.

28. The pacemaker of claim 27, wherein the second cathode electrode comprises an electrically conductive surface of the shaft proximal to the first electrode.

29. The pacemaker of claim 27, wherein the assembly further comprises an exposed surface and the second cathode electrode resides along the exposed surface.

30. The pacemaker of claim 29, wherein the second cathode electrode comprises a plurality of electrodes distributed along the exposed surface.

31. The pacemaker of claim 30, wherein the plurality of electrodes are individually selectable by the pacing circuit.

32. The pacemaker of claim 21, wherein the second cathode electrode extends circumferentially around the assembly, and wherein the second cathode electrode is coupled to the pacing circuit.

33. The pacemaker of claim 21, wherein the dart electrode is at least 3 millimeters long and up to 12 mm long and has tissue-piercing distal tip with a maximum diameter of 1 millimeter.

34. The pacemaker of claim 21, wherein the assembly further comprises a second dart electrode comprising a second shaft having a normally straight position and an electrode carried by the second shaft.

35. An intracardiac pacemaker system, comprising:
   an elongated housing having a proximal end and a distal end;
   a pacing circuit enclosed by the elongated housing;
   a dart electrode coupled to the distal end of the housing and configured to pierce cardiac tissue, the dart electrode comprising:
      a shaft having a normally straight position extending away from the housing distal end;
      an electrical conductor extending through the shaft; and
      a first electrode carried by the shaft, the first electrode being electrically coupled to the pacing circuit via the electrical conductor, wherein the first electrode is a first cathode electrode;
   a fixation member that extends from the elongated housing at a location that is peripheral from the shaft and configured to fix the elongated housing at an implant site within a heart;
   a housing-based electrode carried by the housing proximal to the distal end of the elongated housing, wherein the housing-based electrode is an anode electrode;
   a second cathode electrode proximal to the first cathode electrode;
   a sensing circuit;
   a control circuit,
   wherein the pacing circuit is configured to deliver pacing pulses to ventricular myocardium using the first cathode electrode and the housing-based anode electrode and configured to deliver pacing pulses to the atrial myocardium using the second cathode electrode and the housing-based anode electrode,
   wherein the sensing circuit is configured to sense ventricular electrical events from a first cardiac electrical signal received via the first cathode electrode and the housing-based anode electrode and configured to sense atrial electrical events from a second cardiac electrical signal received via the second cathode electrode and the housing-based anode electrode, and
   wherein the control circuit is coupled to the sensing circuit and the pacing circuit and configured to control the pacing circuit to deliver atrial pacing pulses via the second cathode electrode and the housing-based anode electrode and deliver ventricular pacing pulses via the first cathode electrode and the housing based anode electrode; and
   a delivery tool comprising a receptacle for receiving the housing and advancing the dart electrode to the implant site.

36. A method for using an intracardiac pacemaker, the intracardiac pacemaker comprising:
   an elongated housing having a proximal end and a distal end;
   a pacing circuit enclosed by the elongated housing;
   a sensing circuit;
   a control circuit;
   a dart electrode coupled to the distal end of the elongated housing configured to pierce cardiac tissue, the dart electrode comprising:
      a shaft having a normally straight position extending away from the housing distal end, wherein the shaft is configured to resist bending when subjected to an axial force;
      an electrical conductor extending through the shaft; and
      a first electrode carried by the shaft, the first electrode being electrically coupled to the pacing circuit via the electrical conductor, wherein the first electrode is first cathode electrode;
   a fixation member that extends from the elongated housing at a location that is peripheral from the shaft and configured to fix the elongated housing at an implant site within a heart;
   a housing-based electrode carried by the elongated housing, wherein the housing-based electrode is an anode electrode; and
   a second cathode electrode proximal to the first cathode electrode,
   wherein the pacing circuit is configured to deliver pacing pulses to ventricular myocardium using the first cathode electrode and the housing-based anode electrode and configured to deliver pacing pulses to the atrial myocardium using the second cathode electrode and the housing-based anode electrode,
   wherein the sensing circuit is configured to sense ventricular electrical events from a first cardiac electrical signal received via the first cathode electrode and the housing-based anode electrode and configured to sense atrial electrical events from a second cardiac electrical signal received via the second cathode electrode and the housing-based anode electrode, and
   wherein the control circuit is coupled to the sensing circuit and the pacing circuit and configured to control the pacing circuit to deliver atrial pacing pulses via the second cathode electrode and the housing-based anode electrode and deliver ventricular pacing pulses via the first cathode electrode and the housing based anode electrode, the method comprising:
   deploying the dart electrode at an implant site along a first cardiac chamber of a heart;

deploying the distal fixation member at the implant site and producing a longitudinal pulling force that pulls the distal end of the housing toward the implant site; and advancing the dart electrode into myocardial tissue of a second cardiac chamber different than the first cardiac chamber as the distal fixation member is deployed using the longitudinal pulling force.

\* \* \* \* \*